US010590092B2

(12) United States Patent
Van Summeren et al.

(10) Patent No.: US 10,590,092 B2
(45) Date of Patent: Mar. 17, 2020

(54) PROCESS FOR THE MANUFACTURE OF ISAVUCONAZOLE OR RAVUCONAZOLE

(71) Applicant: Basilea Pharmaceutica AG, Basel (CH)

(72) Inventors: Ruben Van Summeren, Weert (NL); Harrie Vaessen, Wijnandsrade (NL); Daniel Mink, Eupen (BE); Mario Waser, Leonding (AT)

(73) Assignee: Basilea Pharmaceutica AG, Basel (CH)

( * ) Notice: Subject to any disclaimer, the term of this patent is extended or adjusted under 35 U.S.C. 154(b) by 0 days.

(21) Appl. No.: 15/700,647

(22) Filed: Sep. 11, 2017

(65) Prior Publication Data
US 2019/0077771 A1 Mar. 14, 2019

Related U.S. Application Data

(62) Division of application No. 14/419,153, filed as application No. PCT/EP2013/066071 on Jul. 31, 2013, now Pat. No. 9,783,508.

(30) Foreign Application Priority Data

Aug. 7, 2012 (EP) .................................... 12179540

(51) Int. Cl.
*C07D 249/08* (2006.01)

(52) U.S. Cl.
CPC .................................. *C07D 249/08* (2013.01)

(58) Field of Classification Search
CPC .................................................... C07D 249/08
See application file for complete search history.

(56) References Cited

U.S. PATENT DOCUMENTS

| 5,134,152 A | 7/1992 | Takeshiba et al. |
| 8,222,281 B2 | 7/2012 | Toda et al. |
| 8,377,923 B2 | 2/2013 | Yoshimura et al. |

FOREIGN PATENT DOCUMENTS

| EP | 0199474 | | 10/1986 |
| JP | 4208269 | * | 4/1992 |
| JP | H04-208269 A | | 7/1992 |
| WO | 9217474 | | 10/1992 |
| WO | 9902524 | | 1/1999 |
| WO | 2003/002498 A1 | | 1/2003 |
| WO | 2011042827 A1 | | 4/2011 |
| WO | 2011145669 A1 | | 11/2011 |

OTHER PUBLICATIONS

Porter, Resolution of Chiral Drugs, 1991, Pure & Appl. Chem, vol. 63, No. 8, p. 1119-1121 (Year: 1991).*
The International Search Report and Written Opinion, dated Oct. 7, 2013, in the related PCT Appl. No. PCT/EP13/66071.
The extended European search report, dated Oct. 30, 2012, in the related European Appl. No. 12179540.5.
Yu et al., "Asymmetric zinc-Reformatsky reaction of Evans chiral imide with acetophenones and its application to the stereoselective synthesis of triazole antifungal agents," Tetrahedron Asymmetry, vol. 18, No. 8, pp. 949-962, May 16, 2007.
U.S. Office Actions, dated Oct. 8 and Dec. 22, 2015, May 16, Oct. 11 and Dec. 8, 2016, Apr. 5, Jun. 12 and Jul. 6, 2017, respectively, in the parent U.S. Appl. No. 14/419,153.
Chollet et al., "A Convenient Synthesis of β-Hydroxyesters from Andehydes or Ketones and α-Bromoesters BrCH2-Coor', R' Being a Long Carbon Chain," Synthetic Communications, 1989, vol. 19, No. 11 & 12, p. 2167-2173.
Pamies et al., "Chemoenzymatic dynamic kinetic resolution," Trends in Biotechnology, vol. 22, No. 3, Mar. 2004, pp. 130-135.

* cited by examiner

*Primary Examiner* — Karen Cheng

(57) ABSTRACT

The invention relates to a process for the manufacture of diastereomerically and enantiomerically enriched triazole compounds isavuconazole and ravuconazole, comprising a Reformatsky reaction between a ketone and a 2-halozinc-propionate ester, followed by a resolution step, preferably an enzymatic resolution with an esterase enzyme.

3 Claims, No Drawings
Specification includes a Sequence Listing.

PROCESS FOR THE MANUFACTURE OF ISAVUCONAZOLE OR RAVUCONAZOLE

This application is a Divisional of U.S. patent application Ser. No. 14/419,153, filed Feb. 2, 2015, which is a National Stage Application of PCT/EP2013/066071, Jul. 31, 2013, which claims priority from European Patent Application 12179540.5, filed Aug. 7, 2012.

The instant application contains a Sequence Listing which has been submitted electronically in ASCII format and is herein incorporated by reference in its entirety. Said ASCII copy, created on Jan. 31, 2020, is named SequenceListing.txt and is 77 KB in size.

The invention relates to a process for the manufacture of a diastereomerically and enantiomerically enriched ester intermediate for isavuconazole or ravuconazole.

Isavuconazole and ravuconazole are triazole antifungal compounds. Processes for the manufacture of isavuconazole and ravuconazole were disclosed in patents WO99/45008, WO2007/062542 and WO03/002498 to Basilea. In WO2011/042827 a process for the manufacture of enantiomerically pure antifungal azoles such as ravuconazole and isavuconazole is disclosed, wherein a classical resolution of a racemic mixture is performed by the addition of an enantiopure chiral acid, then collection of the desired diastereomer followed by conversion of the salt into the enantiomerically pure form of the desired compound by treatment with a base or an ion-exchange resin. The disadvantages of using such classical resolution are that the chiral auxiliary needs to be applied in near stoichiometric amounts, and that additional process steps are required for recovery of these relatively high amounts of chiral reagent as well as for converting the salt into the free enantiopure product.

Therefore, it is the object of the present invention to provide an improved process for the manufacture of isavuconazole or ravuconazole with high diastereomeric and enantiomeric excess (d.e. and e.e. respectively).

"Enantiomerically enriched" as defined herein is equivalent to the term "optically active" and means that one of the enantiomers of a compound is present in excess compared to the other enantiomer. This excess will hereinafter be referred to as "enantiomeric excess" or e.e. (as for example determined by chiral GC or HPLC analysis). The enantiomeric excess e.e. is equal to the difference between the amounts of enantiomers divided by the sum of the amounts of the enantiomers, which quotient can be expressed as a percentage after multiplication by 100.

"Diastereomerically enriched" means that one of the diastereomers of a compound is present in excess compared to the other diastereomer. This excess will hereinafter be referred to as "diastereomeric excess" or d.e. Similarly, diastereomeric excess d.e. is equal to the difference between the amounts of diastereomers divided by the sum of the amounts of the diastereomers, which quotient can be expressed as a percentage after multiplication by 100.

The invention now relates to a process for the manufacture of diastereomerically enriched compounds according to formula (I),

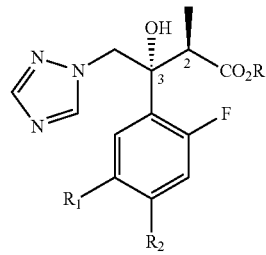

(I)

wherein $R_1$ and $R_2$ are each fluoride or hydrogen and when $R_1$ is fluoride, $R_2$ is hydrogen and when $R_2$ is fluoride, $R_1$ is hydrogen, wherein R is a $C_1$-$C_{12}$ alkyl, a $C_5$-$C_{12}$ aryl or a $C_6$-$C_{11}$ aralkyl, which comprises the steps:

(i) preparation of a 2-halozinc propionate ester according to formula (II)

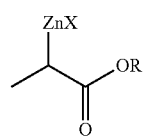

(II)

wherein X is bromide, iodide or chloride, in the presence of a solvent, at a temperature below the boiling temperature of the solvent, (ii) introduction of a ketone according to formula (III)

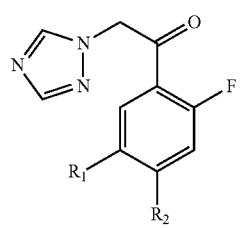

(III)

(iii) a Reformatsky reaction between the 2-halozincpropionate ester according to formula (II) and the ketone according to formula (III) in the presence of a solvent, removal of the excess of zinc, resulting in a precipitate of the desired (2R,3R)/(2S,3S)-diastereomers of the ester according to formula (I), wherein the sequence in which steps (i) and (ii) are performed can be interchanged.

More specifically, the present invention relates to a process for the manufacture of a mixture of diastereomers of a 3-hydroxy-2-methyl-4-[1,2,4]triazol-1-yl-3-phenyl-butyric acid ester derivative according to formula (I):

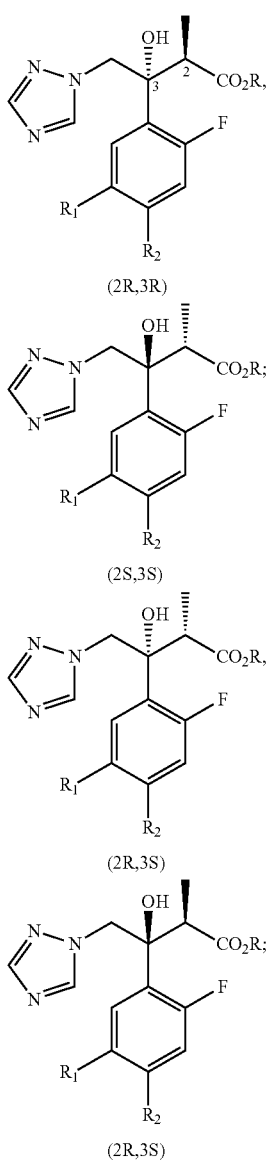

(2R,3R)

(2S,3S)

(2R,3S)

(2R,3S)

which is enriched in the corresponding (2R,3R)/(2S,3S) racemate, and
wherein $R_1$ and $R_2$ are each fluoride or hydrogen and when $R_1$ is fluoride, $R_2$ is hydrogen and when $R_2$ is fluoride, $R_1$ is hydrogen, wherein R is a $C_1$-$C_{12}$ alkyl, a $C_5$-$C_{12}$ aryl or a $C_6$-$C_{11}$ aralkyl,
which comprises steps
(i) preparation of a 2-halozinc propionate ester according to formula (II)

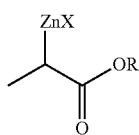

(II)

wherein X is bromide, iodide or chloride,
in the presence of a solvent,
at a temperature below the boiling temperature of the solvent, (ii) introduction of a ketone according to formula (III)

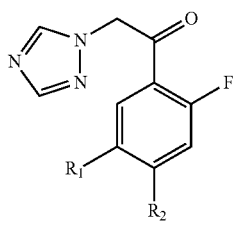

(III)

(iii) performing a Reformatsky reaction between the 2-halozincpropionate ester according to formula (II) and the ketone according to formula (III), in the presence of a solvent,
allowing the resulting reaction mixture to form a precipitate by leaving the mixture stand, with or without stiffing, for more than 0.5 hours preferably for more than 2 hours, after addition of the last reagent to the mixture, wherein the precipitate is enriched in racemic (2R,3R)/(2S,3S) ester according to formula (I), and
separating said precipitate,
wherein the sequence in which steps (i) and (ii) are performed can be interchanged and wherein the excess of zinc is removed before formation of said precipitation.

Surprisingly, this Reformatsky type reaction leads to diastereomerically enriched isavuconazole and ravuconazole. In comparison with the methods of the prior art, the process according to the invention requires simple reactants and conditions and delivers the desired isomer in high yield.

In EP0199474 the Reformatsky reaction was applied for the manufacture of triazole compounds. It was disclosed that these compounds can be obtained in the form of racemic mixtures and that these mixtures can be separated into the individual isomers by methods known in the art. However, successful enzymatic resolution of the racemic ester obtained with the Reformatsky reaction requires the ester to be scalable and cost-efficiently produced in a high diastereomeric purity. The esters obtained from Reformatsky reactions as disclosed in EP0199474 do not fulfil that requirement, as has been demonstrated in comparative example B of this application. Surprisingly, we have found that applying a Reformatsky reaction wherein the Reformatsky reagent 2-halozincpropionate ester is obtained at a temperature below the boiling temperature of the solvent and then allowing precipitation according to the present invention provides direct access to the desired diastereomer of ester (I) in a very high d.c. (>97%) in a single step.

An alternative method for the preparation of the racemic ester (I) is a coupling reaction using an organic lithium salt. For example, WO9217474 discloses a method for preparing ester (I) ($R_2$ is F) through a lithium diisopropylamide (LDA) mediated coupling of ethylpropionate to ketone (III) ($R_2$ is F) at −70° C. Column chromatography was applied to separate the two diastereomers that are formed in the reaction (d.e. not reported), which is considered to be an inefficient and expensive purification method on large scale. Similar results were obtained in-house (see comparative example A): when ethylpropionate was coupled to ketone (III) ($R_1$ is F) in the presence of LDA at −78° C. the desired ester (I) ($R_1$ is F) was isolated in 61% yield with a poor diastereomeric excess (d.e.) of 29%. Hence, in view of a) the poor diastereoselectivities and the concomitant low yields of the reaction;
b) the absence of a cost-efficient and scalable method to increase the d.e. after the reaction and
c) the use of anhydrous conditions at low temperature which is associated with high costs coupling reactions involving strong bases such as LDA (LiHMDS etcetera) do not provide an industrially relevant entry into esters of the general structure (I).

Diastereomeric excess measured after the Reformatsky reaction of the process according to the invention varies from 50 to 60% d.e. After precipitation the product is isolated with diastereomeric excesses varying between 97% and 99.9% d.e.

The product obtained after step (iii) of the process according to the invention can be resolved to according to any known method, including e.g. diastereomeric crystallization of the ester mixture after saponification of the ester and reaction of the obtained acid mixture with an optically pure base like 1-phenylethylamine or 2-amino-1-butanol, or chiral HPLC.

Subsequent enzymatic resolution of the (2R,3R)/(2S,3S)-ester (I) with an esterase enzyme is however preferred because it leads to a particularly attractive industrially scalable route to isavuconazole or ravuconazole with d.e.'s of more than 99% and e.e.'s of more than 99%. Such an enzymatic resolution approach has never been reported for (intermediates towards) triazole-based anti-fungal agents despite the fact that this class of compounds has been in the centre of attention of the pharmaceutical industry for over 3 decades and despite the fact that enzymatic resolution is a technology that is otherwise frequently employed in pharmaceutical processes. Also a very recent patent application in the field (WO2011/042827), which has the resolution step as the main subject of the invention, discloses classical resolutions only and not enzymatic resolution. Possibly, the relatively demanding steric properties of triazole-based anti-fungal agents make them challenging substrates for enzymes in general. It is clearly not straightforward to find a suitable enzyme for this type of substrate. In fact over 200 hydrolytic enzymes were screened for the process according to the invention and only one type of enzyme family (i.e. esterases) provided both activity as well as selectivity towards esters of the general formula (I).

In summary, the industrial preparation of the anti-fungal agents isavuconazole and ravuconazole requires efficient and scalable methods for the introduction of both diastereo- as well as enantioselectivity. The herein reported diastereoselective Reformatsky-precipitation protocol in conjunction with the enzymatic resolution procedure provides both.

In a preferred embodiment of the present invention, formula (I) represents the ester intermediate for isavuconazole. When $R_1$ is fluoride and $R_2$ is hydrogen in formula (I), the ester intermediate for isavuconazole is represented. When $R_1$ is hydrogen and $R_2$ is fluoride in formula (I), the ester intermediate for ravuconazole is represented.

R in the 2-halozincpropionate ester according to formula (II) can be a branched or unbranched alkyl, a $C_1$-$C_{12}$ aryl or a $C_6$-$C_{11}$ aralkyl, preferably a branched or unbranched $C_1$-$C_8$ alkyl or $C_5$-$C_8$ aryl, more preferably a branched or unbranched $C_1$-$C_4$ alkyl. A branched or unbranched $C_1$-$C_4$ alkyl can be any one from methyl, ethyl, n-propyl, i-propyl, n-butyl, sec-butyl, tert-butyl. An example for the aryl-2-halozincpropionate ester is phenol-2-halozincpropionate ester. Preferably, R is methyl or ethyl, more preferably R is ethyl.

X in the 2-halozincpropionate ester according to formula (II) can be any one from bromide, iodide or chloride. More preferably X is bromide.

In an embodiment of the present invention, R in formula (II) is ethyl and X in formula (II) is bromide.

The temperature applied in the Reformatsky reaction according to the invention and more specifically in the manufacture of the 2-halozincpropionate ester is at best low and may vary between −30° C. and the boiling temperature at atmospheric pressure of the solvent applied. At least the temperature is below the boiling temperature of the solvent at atmospheric pressure. At higher temperatures the formation of Reformatsky reagent is hampered, for example because of homocoupling of the esters with concomitant release of zinc salts that inhibit the reaction, therewith preventing full conversion and influencing the precipitation. Preferably, the temperature is between −30° C. and 85° C., more preferably between −10° C. and 40° C. and most preferably between −10° C. and 10° C. Even more preferably, the temperature is close to 0° C., e.g. between −2° C. and 2° C.

Accordingly, the temperature applied in step (i) of the process according to the invention may vary between −30° C. and the boiling temperature at atmospheric pressure of the solvent applied. Preferably, the temperature in step (i) is below the boiling temperature of the solvent at atmospheric pressure. More preferably, the temperature in step (i) is between −30° C. and 85° C., yet more preferably between −10° C. and 40° C. and most preferably between −10° C. and 10° C. Even more preferably, the temperature in step (i) is close to 0° C., e.g. between −2° C. and 2° C.

Furthermore, the temperature applied in step (iii) of the process according to the invention may preferably vary between −30° C. and the boiling temperature at atmospheric pressure of the solvent applied. More preferably, the temperature in step (iii) is below the boiling temperature of the solvent at atmospheric pressure. Even more preferably, the temperature in step (iii) is between −30° C. and 85° C., most preferably between −10° C. and 40° C. and even more preferably between 10° C. and 30° C. Still more preferably, the temperature in step (iii) is at room temperature, e.g. between 15° C. and 25° C.

The solvents applied in steps (i) and (iii) of the process of the invention are aprotic solvents. Preferably, the solvents are polar aprotic solvents. To the alternative apolar aprotic solvents are used in combination with polar aprotic solvents. Suitable solvents are tetrahydrofuran, 2-methyl-tetrahydrofuran, tertbutylmethylether, di-isopropylether, di-ethylether, acetonitrile, ethylacetate, dichloromethane or toluene. Preferred solvents in steps (i) and (iii) of the process of the invention are independently tetrahydrofuran and 2-methyl-tetrahydrofuran.

The solvents applied in steps (i) and (iii) of the process according to the invention can be the same or different. More preferably, the solvents applied in steps (i) and (iii) of the process according to the present invention are the same. Even more preferable the solvent in steps (i) and (iii) is tetrahydrofuran or 2-methyl-tetrahydrofuran.

The 2-halozincpropionate ester can be obtained via a reaction between a 2-halopropionate ester and metallic zinc. Activation of zinc is described by Fürstner (Chapter 14, The Reformatsky reaction in Organozinc Reagents, Knochel and Jones, Oxford University Press, p 287-305, 1999). The zinc applied in the process according to the invention can advantageously be activated by acid or iodine treatment of zinc or by reductive treatment of a zinc salt. Reductive treatment of a zinc salt can be done with for example lithium, sodium, potassium or diisobutylaluminiumhydride.

Furthermore, the particle size of the metallic zinc applied in the process according to the invention is preferably as small as possible. Smaller particles provide larger surface areas, thus enhancing the interactions in the reaction. Preferably, the zinc particles have a diameter smaller than 50 µm, more preferably smaller than 10 µm, even more preferably smaller than 5 µm. Zinc particles of these sizes are often referred to as zinc dust. In combination with the solvent, the zinc is often present as a suspension in the process according to the invention. This suspension can be stirred during the Reformatsky reaction.

In the reaction between a 2-halopropionate ester and metallic zinc, the zinc is applied in 1 to 3 molar equivalents relative to the 2-halopropionate, preferably in 1 to 2 molar equivalents, more preferably in 1 to 1.2 molar equivalents relative to the 2-halopropionate.

In the alternative, the 2-halozincpropionate ester according to formula (II) can be obtained via a reaction of the 2-halopropionate ester with a dialkyl zinc reagent in the presence of a suitable metal catalyst. As an example diethyl zinc and nickel (II) acetalacetonate as described by Yang et al in Tetrahedron: *Asymmetry* (2007, 18, 949-962) can be employed.

In step (iii) of the process according to the reaction, anhydrous conditions are preferred. Such conditions can be obtained by working under inert atmosphere, e.g. by applying nitrogen or argon. In an inert atmosphere according to the invention as little as possible water is present. The atmosphere is inert in that it is non-reactive in the chemical synthesis according to the invention.

In the process according to the invention, the sequence of preparation of the ester according to formula (II) (step (i)) and addition of the ketone according to formula (III) (step (ii)) can be interchanged. In one embodiment of the invention, the ketone was added after the 2-halopropionate ester had reacted with the zinc to form the Reformatsky reagent (WO2009035684). In the alternative, the ketone is already present and the reactants for preparation of the 2-halozincpropionate ester are added afterwards (Barbier conditions). The excess of zinc is removed after completion of step (i) and before the precipitation starts. The removal of excess of zinc can be done by filtering off.

After the Reformatsky reaction, the desired diastereomer of the ester according to formula (I) is allowed to precipitate. One of the factors in allowing the ester to precipitate is leaving the reaction mixture stand for a certain period of time. Preferably the reaction is left for more than 12 hours after the addition of the last reagent, more preferably for more than 6 hours, even more preferably for more than 2 hours and most preferably for more than 0.5 hour. During the waiting time, stirring of the reaction mixture can proceed as before. Precipitation can be enhanced by addition of a small amount of precipitate containing desired diastereomer, which was obtained before. Furthermore, precipitation can be stimulated and yield can be improved by addition of a non-protic apolar solvent such as tertbutylmethylether or n-heptane.

The precipitate obtained in step (iii) of the process according to the invention is isolated through filtration. Subsequently the desired diastereomer of the ester (I) is obtained by extraction into an organic solvent such as ethyl acetate. Advantageously, this extraction involves treatment with an aqueous acidic solution. Optionally, the organic solution containing the ester (I) is concentrated to give a solid prior to the subsequent enzymatic resolution step.

Particularly preferred is a process according to the present invention, wherein the esterase enzyme used for resolution is an isolated polypeptide with esterase activity comprising an amino acid sequence shown in SEQ ID No. 4 or a homologue thereof having an amino acid identity of at least 90%.

SEQ ID No. 4:
MGQPASPPVVDTAQGRVLGKYVSLEGLAQPVAVELGVPFAKPPLGSLRF

APPQPAEPWSFVKNTTSYPPMCCQEPIGGQMLSDLFTNRKERLIPEFSE

DCLYLNIYTPADLTKRGRLPVMVWIHGGGLVVGGASTYDGLALAAHENV

VVVAIQYRLGIWGFFSTGDEHSRGNWGHLDQVAALHWVQENIANFGGDP

GSVTIEGESAGGESVSVLVLSPLAKNLFHRAISESGVAFTAGLVRKDMK

AAAKQIAVLAGCKTTTSAVFVHCLRQKSEDELLDLTLKMKFFALDLHGD

PRESHPFLTTVVDGVLLPKMPEEILAEKDFNTVPYIVGINKQEFGWLLP

TMMGFPLSEGKLDQKTATSLLWKSYPIANIPEELTPVATDKYLGGTDDP

VKKKDLFLDLMGDVVFGVPSVTVARQHRDAGAPTYMYEEQYRPSESSDK

KPKTVIGDHGDEIFSVFGFPLLKGDAPEEEVSLSKTVMKFWANFARSGN

PNGEGLPHWPMYDQEEGYLQIGVNTQAAKRLKGEEVAFWNDLLSKEAAK

KPPKIKHAEL

The esterase shown in SEQ ID Nr. 4 and homologues thereof are described in WO2009/004039 and WO2010/122175.

Preferably, said esterase enzyme has at least 95% identity with SEQ ID NO 4, more preferably at least 97%, even more preferably at least 98% and most preferably more than 99% identity with SEQ ID No. 4.

Even more preferred is a process according to the present invention, wherein the esterase enzyme is an isolated polypeptide with esterase activity comprising an amino acid sequence shown in SEQ ID No. 2 or a homologue thereof having an amino acid identity of at least 90%, which homologue contains valine as amino acid in position 239 of said sequence or the position corresponding thereto.

SEQ ID No. 2:
MGQPASPPVVDTAQGRVLGKYVSLEGLAQPVAVFLGVPFAKPPLGSLRF

APPQPAEPWSFVKNTTSYPPMCCQEPIGGQMLSDLFTNRKERLIPEFSE

DCLYLNIYTPADLTKRGRLPVMVWIHGGGLVVGGASTYDGLALAAHENV

VVVAIQYRLGIWGFFSTGDEHSRGNWGHLDQVAALHWVQENIANFGGDP

GSVTIFGESAGGESVSVLVLSPLAKNLFHRAISESGVALTAGVVRKDMK

AAAKQIAVLAGCKTTTSAVFVHCLRQKSEDEILDLTLKMKFFALDLHGD

PRESHPFLTTVVDGVLLPKMPEEILAEKDFNTVPYIVGINKQEFGWLLP

TMMGFPLSEGKLDQKTATSLLWKSYPIANIPEELTPVATDKYLGGTDDP

VKKKDLFLDLMGDVVFGVPSVTVARQIIRDAGAPTYMYEFQYRPSFSSD

KKPKTVIGDHGDEIFSVFGFPLLKGDAPEEEVSLSKTVMKFWANFARSG

NPNGEGLPHWPMYDQEEGYLQIGVNTQAAKRLKGEEVAFWNDLLSKEAA

KKPPKIKHAEL

The mutation of the esterase enzyme of SEQ ID No. 4 (APLE) by replacing leucine in position 239 of said sequence with valine is known from WO 2010/122175.

As is known, the numbering of amino acids is dependent on the species the protein originates from. The numbering can also change as a result of deletions or insertions. It is known, however, to a skilled person how to align sequences. Thus, for the purposes of this application, the phrase "or corresponding thereto" is used to describe amino acid positions that except for the number are the same as the position 239 in SEQ ID No. 2.

Preferably, the esterase enzyme has at least 95% identity with SEQ ID NO 2, more preferably at least 97%, even more preferably at least 98% and most preferably more than 99% identity with SEQ ID NO 2.

Enzymes belonging to this category are mostly pig liver esterases or variants thereof. Therefore, in an embodiment, the invention also relates to the process according to the invention wherein the enzymatic resolution in step (iv) is performed by pig liver esterases or variants thereof, in particular by an esterase enzyme of SEQ ID NO 2 or 4, most preferably SEQ ID NO 2.

In the present application "an esterase having at least 90% sequence identity to the amino acid sequence of (a reference sequence)" means that such protein is a homologue of the respective reference sequence having an amino acid sequence, which is for at least 90% identical to the amino acid sequence of the reference sequence as determined in sequence alignments performed with sequence alignment tools such as BLASTP (http://blast.ncbi.nlm.nih.gov/Blast), ClustalW (http://www.ebi.ac.uk/Tools/clustalw2) or Align Plus 5 (Scientific & Educational Software, Cary, N.C., USA).

For the purposes of the present application, the term homologue is also meant to include nucleic acid sequences (polynucleotide sequences) which differ from another nucleic acid sequence due to the degeneracy of the genetic code and encode the same polypeptide sequence.

Sequence identity or similarity is herein defined as a relationship between two or more polypeptide sequences or two or more nucleic acid sequences, as determined by comparing the sequences. Usually, sequence identities or similarities are compared over the whole length of the sequences, but may however also be compared only for a part of the sequences aligning with each other. In the art, "identity" or "similarity" also means the degree of sequence relatedness between polypeptide sequences or nucleic acid sequences, as the case may be, as determined by the match between such sequences. Preferred methods to determine identity or similarity are designed to give the largest match between the sequences tested. In context of this invention a preferred computer program method to determine identity and similarity between two sequences includes BLASTP and BLASTN (Altschul, S. F. et al., *J. Mol. Biol.* 1990, 215, 403-410, publicly available from NCBI and other sources (BLAST Manual, Altschul, S. et al., NCBI NLM NIH, Bethesda, Md., USA). Preferred parameters for polypeptide sequence comparison using BLASTP are gap open 10.0, gap extend 0.5, Blosum 62 matrix. Preferred parameters for nucleic acid sequence comparison using BLASTN are gap open 10.0, gap extend (15, DNA full matrix (DNA identity matrix).

In the enzymatic resolution according to the invention several reaction parameters can be varied such as solvent, co-solvent, pH, temperature, and substrate concentration in order to optimize the reaction.

Generally the solvent can be a mixture of water with a water-miscible solvent, for example with an alcohol such as methanol, ethanol, isopropanol or tert-butanol, or with dioxane, tetrahydrofuran, acetone or dimethyl sulfoxide or a two-phase system of water and of a water-immiscible solvent, for example an aromatic compound such as toluene or xylene, an alkane such as n-hexane, n-heptane or cyclohexane, or an ether such as diisopropyl ether or methyl tert-butyl ether.

The nature of the co-solvent in the enzymatic resolution according to the invention plays a crucial role, since for example no conversion was observed when 2-methyltetrahydrofuran was used. Preferably tort-butanol, tert-butylacetate, methylisobutylketone or toluene are used as co-solvent. More preferably, toluene is used as co-solvent for the enzymatic resolution.

The effect of pH on the enzymatic activity is not critical. The pH of the reaction solution is between 4 and 11, preferably between 6 and 9. However, more preferably the pH optimum for the enzymatic resolution according to the invention lies in the range between pH 7.5 and 8.

The reaction temperature for the conversion of the invention is normally between 0 and 90° C., preferably between 10 and 60° C. The enzymatic resolution reaction according to the invention is faster at higher temperatures. However, the enzyme activity decreases over time at 37° C. Therefore, the temperature during the enzymatic resolution reaction is more preferably between 28 and 37° C.

Substrate concentrations for the enzymatic resolution can vary from 0.1 to 50 weight percentage, preferably from 1 to 25 weight percentage, more preferably from 2 to 10 weight percentage. Most preferably, the substrate concentration is between 4 and 6 weight percentage.

The esterase according to this invention may be used in any form. The esterase may be used for example in the form of a dispersion, a solution or in immobilized form. Furthermore, the esterase may be used for example as crude enzyme, as a commercially available enzyme, as an enzyme further purified from a commercially available preparation, as an enzyme obtained from its source by a combination of known purification methods, in whole (optionally permeabilized and/or immobilized) cells that naturally or through genetic modification possess the required esterase activity, or in a lysate of cells with such activity.

After the enzymatic resolution step, product isolation can take place by conventional methods such as extraction, crystallization, column chromatography and/or distillation.

The ester obtained after step (iv) of the process according to the invention can be converted to the corresponding amide through methods known in the art, e.g. through treatment with ammonia. Subsequently, the amide is further converted to isavuconazole or ravuconazole via known methods, e.g. as was disclosed in WO03/002498. The amide can be dehydrated into the corresponding cyanide and the cyanide can be converted into the corresponding thioamide through e.g. reaction with a sulfide salt such as ammonium sulfide and finally the thioamide can be converted into isavuconazole or ravuconazole via reaction with an appropriately substituted 4-cyanoacetophenone reagent such as e.g. α-bromo-4-cyanoacetophenone.

The invention further relates to all possible combinations of different embodiments and/or preferred features according to the process according to the invention as described herein.

The invention will be elucidated with reference to the following examples, without however being restricted by these:

EXAMPLES

Diastereomeric Excess of Ester (I) was Determined by GC:
GC: HP-5 column (30 m×0.32 mm×0.25 μm); Init. Temp.: 50° C., 0 min., 20° C./min to 150° C., 150° C. for 0 min.; 10° C./min to 190° C., 190° C. for 2 min.; 20° C./min to 300° C., 300° C. for 0 min.; Retention times: 2.06 min.: ethyl-propionate; 3.25 min.: ethyl-2-bromopropionate; 9.17 min.: ketone II ($R_1$=F); 12.82 min.: RS/SR-ester I; 12.90 min.: RR/SS-ester I $^1$H-NMR of RR/SS-ester I (CDCl$_3$, 300 MHz) δ=1.04 (d, J=7.2 Hz, 3H), 1.34 (t, J=7.2 Hz, 3H), 3.30 (q, J=7.2 Hz, 1H), 4.25 (q, J=7.2 Hz, 2H), 4.60 (d, J=14.1 Hz, 1H), 4.89 (d, J=14.4 Hz), 6.95 (m, 2H), 7.20 (m, 1H), 7.75 (s, 1H), 8.11 (s, 1H) ppm.

$^1$H-NMR of RS/SR-ester I (CDCl$_3$, 300 MHz) δ=0.98 (t, J=7.2 Hz, 3H), 1.41 (d, J=7.2 Hz, 3H), 3.37 (q, J=7.2 Hz, 1H), 3.95 (m, 2H), 4.61 (d, J=13.8 Hz, 1H), 4.83 (d, J=14.1 Hz), 6.97 (m, 3H), 7.71 (s, 1H), 8.08 (s, 1H) ppm.

Comparative Example A: Preparation of Racemic Ester (I) by Organolithium Coupling a) Preparation of a Stock-solution of lithium-diisopropyl-amide (LDA) in tetrahydrofuran (THF):
Diisopropylamine (716 mg, 7.1 mmol, 1.05 eq) was dissolved in anhydrous THF (21.3 mL) and the resulting solution was cooled to −78° C. under a nitrogen atmosphere. Subsequently, n-BuLi (2.7 M solution in n-heptane, 2.5 mL, 6.7 mmol, 1.0 eq) was added in a drop wise fashion over 15 minutes and the reaction mixture was stirred at −78° C. for an additional 15 minutes. Then the solution was warmed to 0° C. and stirred for 30 minutes after which the stock solution was cooled to −78° C. again.
b) Coupling reaction:
The thus obtained LDA-solution (3.66 mL, 0.98 mmol, 1.1 eq) was transferred to a Schlenk vessel and ethylpropionate (100 mg, 0.98 mmol, 1.1 eq.) was added in a drop wise fashion at −78° C. under a nitrogen atmosphere. The resulting mixture was stirred at −78° C. for 30 minutes and then 1-(2,5-difluorophenyl)-2-(1H-1,2,4-triazol-1-yl)ethanone (200 mg, 0.90 mmol, 1.0 eq.) in THF (3.66 mL) was added in a drop wise fashion over 15 minutes. The reaction mixture was stirred for 2 hours at −78° C. and then quenched with acetic acid and warmed to room temperature. The mixture was diluted with aqueous saturated NH$_4$Cl and ethylacetate. The aqueous layer was extracted with ethylacetate (2×) and the combined organic layers were washed with brine, dried (Na$_2$SO$_4$), filtered and concentrated in vacuo to give a yellow oil containing the racemic ester I with a diastereomeric excess of 29% in favour of the desired RR/SS diastereomer. Further purification by column chromatography (n-heptane/EtOAc/MeOH 60/40/5 v/v/v) provided the RR/SS diastereomer (light yellow solid) as well as the RS/SR diastereomer (off-white solid) in a combined overall yield of 179 mg (0.55 mmol, 61%).

Comparative Example B: Reformatsky Reaction According to Steps (i), (ii) and (iii) at Elevated Temperature with Ketone Already Present (Barbier Conditions)

A 2-neck flask with cooler was charged with zinc (1.1 g, 17 mmol, 3.8 eq.) and heated in vacuo using a hotgun (3 nitogen-vacuum cycles). Subsequently, THF (60 mL) was added and then trimethylsilylchloride (0.15 mL). The resulting suspension was stirred under a nitrogen atmosphere at room temperature for 15 minutes, after which a solution of ketone III ($R_1$=F, 1.0 g, 4.5 mmol, 1.0 eq.) in THF (30 mL) was added. The reaction mixture was then heated to 66° C., after which the heating source was removed. Subsequently, a solution of ethyl-2-bromopropionate (0.87 mL, 1.2 g, 6.7 mmol, 1.5 eq.) in THF (20 mL) was added dropwise over 10 minutes. The reaction mixture was then stirred at 66° C. for 1.5 hours, after which it was cooled to room temperature. The reaction was quenched by addition of a saturated aqueous ammoniumchloride solution (100 mL) and diluted with methyl-tertbutyl ether (MTBE, 100 mL). The layers were separated and the aqueous layer was extracted with MTBE (2×100 mL). The combined organic layers were washed with brine (100 mL), dried (Na$_2$SO$_4$), filtered and concentrated in vacuo to give a yellow oil (1.4 g) containing racemic ester I. $^1$H-NMR- and GC-analysis showed a conversion of ketone III ($R_1$=F) of 80% and a d.e. of ester I of 60% in favor of the desired RR/SS-diastereomer. The product was not purified further.

Example 1: Reformatsky Reaction According to Step (iii) with Pre-formation of Reformatsky Reagent at Low Temperature Followed by Addition to the Ketone a) Preparation of Stock solution of Reformatsky reagent:
A 2-neck flask was charged with zinc (5.8 g, 89 mmol, 2.0 eq.) under a nitrogen atmosphere and anhydrous THF (101 mL) and then trimethylsilylchloride (TMSCl, 1.12 mL) were added. The resulting suspension was stirred at room temperature for 30 minutes and then cooled to 0° C. Subsequently, ethyl-2-bromopropionate (5.8 mL, 8.1 g, 44.7 mmol, 1.0 eq.) was dosed to the suspension in a drop wise fashion over 30 minutes. The reaction mixture was stirred for an additional 15 minutes and then filtered under a nitrogen atmosphere into a Schlenk vessel to remove residual zinc.
Ketone III ($R_1$=F, 1.0 g, 4.5 mmol, 1.0 eq.) was charged into a Schlenk vessel and anhydrous THPF (10 mL) was added under a nitrogen atmosphere. To the resulting solution was added 20 mL of the previously prepared stock solution of Reformatsky reagent (vide supra, 8.36 mmol, 1.9 eq.) in a dropwise fashion over 30 minutes at room temperature while stirring. After completion of the addition the resulting reaction mixture was stirred under a nitrogen atmosphere for 36 hours (clear solution). GC-analysis showed that the ester I ($R_1$=F) had formed with 80% conversion based on ketone III ($R_1$=F) and a d.e. of 60% in favor of the desired RR/SS diastereomer. The reaction mixture was concentrated in vacuo to a volume of 10 mL after which n-heptane was added until formation of a solid was observed. The resulting suspension was stirred for 16 hours after which the solid was isolated through filtration. The solid was then dissolved in a mixture of aqueous HCl (pH=1) and ethyl acetate resulting in a clear biphasic system. The phases were separated and the aqueous layer was extracted with ethyl acetate (2×). The combined organic layers were washed with water and brine, dried (Na$_2$SO$_4$), filtered and concentrated in vacuo to give racemic RR/SS ester I ($R_1$=F) as a light yellow solid with >99% d.e. as determined by GC.

Example 2: Reformatsky Reaction According to Step (iii) with Zinc Removal Prior to Addition of the Ketone Zinc (11.7 g, 179 mmol, 4.0 eq.) was suspended in THF (200 mL) and stirred in the presence of TMSCl (2.25 mL) under a nitrogen atmosphere at ambient temperature for 30 minutes in a 250 mL 3-neck flask. Subsequently, the suspension was cooled to 0° C. and ethyl-2-bromopropionate (11.6 mL, 89.6 mmol, 2.0 eq) was added via a syringe pump over 45 minutes. The reaction mixture was stirred for an additional 15 minutes at 0° C. (conversion checked with GC to be 100%), after which the suspension was filtered via cannula over a glass filter under a nitrogen stream to the reaction vessel (500 mL 3-neck flask). Subsequently, a solution of ketone III ($R_1$=F, 10 g, 44.8 mmol, 1.0 eq.) in THF (130 mL) was dosed to the reaction mixture over 1 hour at room temperature. The mixture was stirred for an additional 72 hours at which point a solid had formed. The suspension was filtered and the off-white solid was suspended in EtOAc and dissolved by addition of water and aqueous HCl until a clear biphasic system was obtained (pH 1). The layers were separated and the aqueous layer was extracted with EtOAc (2×). The combined organic layers were washed with water and brine, dried ($Na_2SO_4$), filtered and concentrated in vacuo to give racemic RR/SS ester I ($R_1$=F, 8.8 g, 27 mmol, 60%) as a light yellow solid with >99% d.e. as determined by GC. The filtrate was subjected to the same aqueous work-up. GC-analysis showed that the remaining ketone was present in the filtrate as well as racemic ester I with a d.e. of −25% (in favor of the undesired RS/SR diastereomer).

Example 3: Reformatsky Reaction According to Step (iii) with Zinc Removal after Addition of the Ketone but Prior to the Start of Precipitation Zinc (98 g, 1.5 mol, 4.0 eq.) was suspended in THF (1.7 L) and mechanically stirred in the presence of TMSCl (18.7 mL) under a nitrogen atmosphere at ambient temperature for 30 minutes. Subsequently, the suspension was cooled to 0° C. and ethyl-2-bromopropionate (96.6 mL, 744 mmol, 2.0 eq) was added via a syringe pump over 1 hour. The reaction mixture was stirred for 15 minutes at 0° C. (conversion checked with GC to be 100%), after which a solution of ketone III ($R_1$=F, 83 g, 372 mmol, 1.0 eq.) in THF (830 mL) was dosed over 20 minutes at room temperature. The mixture was stirred for an additional 15 minutes (conversion checked with GC to be >90%) and then filtered over celite. The d.e. of the reaction mixture was determined to be 60% by GC. Upon stirring of the reaction mixture, a suspension started to form after 5 hours. The suspension was stirred for 88 hours at which point the d.e. of the mother liquid had decreased to −10% (in favor of the undesired RS/SR diastereomer). The suspension was filtered and the off-white solid was washed with MTBE (2×125 mL). The solid was subsequently suspended in EtOAc (2.1 L) and dissolved by addition of water (1.25 L) and aqueous HCl (10% w/w; 76 g) until a clear biphasic system was obtained (pH 1.3). The layers were separated and the organic layer was washed with aqueous HCl (1.1 L, pH 1.1), aqueous $NaHCO_3$ (500 mL containing 0.60 g $NaHCO_3$), water (2×250 mL) and brine (250 mL). The organic layer was then dried ($Na_2SO_4$), filtered and concentrated in vacuo to give racemic RR/SS-ester I (54 g, 167 mmol, 45%) in 97% d.e.

Example 4: Enzymatic Resolution According to Step (iv)

To a potassium phosphate buffer solution (500 mL, 50 mM, pH 7.8) was added a suspension (100 mL) containing the esterase of SEQ ID NO 1 (10 g, whole *Escherichia coli* cells expressing the recombinant esterase gene of SEQ ID NO 1 encoding the esterase of SEQ ID NO 2, prepared as described in WO2010/122175). The pH was adapted to 7.8 and subsequently a solution of racemic RR/SS ester I ($R_1$=F, 40 g, 123 mmol, 97% d.e.) in toluene (400 mL) was added. The resulting mixture was stirred at 28° C. while maintaining the pH at 7.8 via titration with NaOH (1 M, aq.). Analysis by HPLC showed that the e.e. of the R,R-ester I was 98.5% after 22 hours. The reaction was worked-up as described below after 26 hours. N.B. the reaction with S/C-ratio of 2:1 and 3:1 were both finished within 20 hours; e.e of R,R-ester I>99%.

```
SEQ ID NO 1:
ATGGGACAACCAGCTTCGCCGCCTGTCGTTGATACCGCTCAAGGACGAG

TCTTGGGTAAGTACGTCTCTTTAGAGGGATTGGCACAACCGGTTGCTGT

CTTCTTGGGAGTCCCTTTTGCTAAGCCACCTCTTGGATCTTTGAGGTTT

GCCCCGCCGCAACCAGCAGAGCCATGGTCTTTCGTTAAGAACACTACTT

CCTACCCTCCAATGTGTTGTCAAGAACCAATCGGAGGACAAATGCTTTC

AGACCTATTCACTAACAGAAAGGAAAGGCTTATCCCGGAGTTCTCTGAG

GATTGCCTTTACCTAAATATTTACACTCCTGCCGATTTGACAAAGAGGG

GTAGGTTGCCGGTTATGGTTTGGATTCATGGAGGAGGTTTGGTTGTTGG

CGGAGCATCCACTTATGACGGATTGGCTCTTGCCGCGCACGAGAACGTT

GTTGTTGTTGCTATTCAATACCGTTTGGGTATTTGGGGATTTTTCTCCA

CAGGAGATGAGCATTCCCGTGGAAACTGGGGCCATTTAGATCAAGTTGC

TGCATTGCATTGGGTCCAAGAAAACATTGCTAACTTCGGAGGTGATCCA

GGTTCTGTTACTATTTTCGGAGAATCAGCAGGCGGAGAGAGTGTCTCTG

TATTGGTTTTATCACCATTAGCTAAGAACCTTTTTCATCGTGCTATTTC

CGAAAGTGGTGTTGCTTTTACCGCCGGTGTGGTCAGGAAGGATATGAAG

GCCGCAGCCAAGCAGATCGCTGTCCTTGCAGGATGCAAAACTACTACTT

CGGCAGTCTTCGTGCATTGTTTGCGTCAAAAGTCGGAAGATGAACTTTT

AGACCTCACGTTGAAGATGAAATTCTTTGCCCTTGACTTACACGGAGAT

CCAAGGGAATCTCACCCTTTTTTGACCACTGTTGTTGACGGAGTTTTGT

TGCCTAAGATGCCTGAGGAAATCTTGGCCGAGAAGGACTTTAACACCGT

CCCATACATTGTTGGAATTAACAAGCAGGAGTTCGGATGGCTTTTGCCA

ACGATGATGGGATTTCCTCTTTCCGAGGGAAAGTTGGATCAAAAGACGG

CTACGTCACTTTTGTGGAAGTCCTACCCAATTGCCAACATTCCTGAAGA

GTTGACCCCAGTTGCTACCGATAAGTATTTAGGAGGAACAGATGATCCT

GTCAAAAAGAAAGATTTGTTTTTGGATCTGATGGGAGACGTTGTTTTCG

GCGTCCCATCAGTTACGGTTGCTCGTCAGCATAGGGACGCAGGAGCTCC

AACTTACATGTATGAGTTCCAATATCGTCCATCTTTTTCATCGGATAAG

AAACCTAAGACGGTTATTGGAGATCATGGAGACGAAATTTTTTCCGTCT

TCGGCTTCCCATTGCTCAAAGGTGACGCTCCAGAGGAAGAAGTCAGTCT

TTCTAAGACGGTTATGAAATTTTGGGCTAACTTCGCCCGTAGTGGAAAC

CCTAATGGAGAAGGATTGCCTCACTGGCCGATGTACGATCAAGAGGAGG
```

-continued

GATACCTTCAAATTGGTGTCAACACTCAAGCAGCTAAGAGGTTGAAAGG

CGAGGAGGTTGCTTTTTGGAACGACCTGTTGTCCAAGGAAGCAGCAAAG

AAGCCACCTAAGATAAAGCACGCCGAATTGTAA

Work-up:
Dicalite 4208 (20 g) was added to the reaction mixture and the resulting suspension was stirred for 5 minutes. Subsequently, the mixture was filtered over a precoated (dicalite 4108) glass filter. The filter cake was washed with toluene (2×200 mL) and the combined filtrate was separated. At this stage, the toluene layer was slightly emulsified so a second filtration over a precoated filter was performed. The resulting biphasic filtrate was separated and the aqueous layer was added to the earlier obtained aqueous phase. The combined aqueous layers were then extracted with toluene (250 mL) giving a completely emulsified organic phase. The toluene layer was filtered over a precoated filter twice, upon which a clear biphasic system was obtained. The layers were separated and the combined organic layers were washed with aqueous $NaHCO_3$ (100 mL, 5 wt %). Finally, the organic layer was concentrated in vacuo to give R,R-ester I as an off-white solid:
Using the thus obtained protocol, 210 g of racemic RR/SS-ester I (d.e. 97%) was converted in five batches each containing 40-45 grams of starting material. The enantiopure ester R,R-ester I (d.e. 95%; e.e. >99.5%) was isolated in 48% yield (101 g, 311 mmol).
Analysis:
Determination of the e.e. of ester I was done by chiral HPLC. A single method was developed separating the enantiomers of racemic RR/SS-ester I as well as the enantiomers of the corresponding carboxylic acid:
Column Daicel AD, 2×50×4.6 mm ID, particle size: 10 µm, eluent: heptane/MeOH/EtOH 95:2.1:2.9 v/v/v+0.05% trifluoroacetic acid+0.05% diethylamine; runtime: 15 min, Pressure: 10 bars, Flow: 1.8 mL/min, Temperature: 20° C., UV detection at 210 nm. Retention times: SS-enantiomer ester I: 2.15 min.; SS-enantiomer carboxylic acid: 3.02 min; RR-enantiomer carboxylic acid: 4.31 min.; RR-enantiomer ester I: 8.21 min.
The conversion was confirmed by measuring the concentration of both the ester I as well as the carboxylic acid by HPLC:
Column Hypersil BDS-3, 250×4.6 mm ID, particle size, 5 µm, eluent A: 0.15% formic acid and 0.025% triethylamine in Milli-Q; eluent B: 0.15% formic acid and 0.025% triethylamine in acetonitrile, gradient A:B=95:5 (v/v) to 5:95 over 10 min, maintain at 5:95 for 5 min, to 95:5 over 3 min, maintain at 95:5 for 5 min (t=23 min). Flow: 1.0 mL/min, temperature: 40° C., UV detection at 210 nm. Retention times: carboxylic acid: 9.55 min.; ester I 12.35 min.

Example 5: Enzyme Screening

In a screening of more than 200 hydrolase enzymes (lipases, esterases, proteases) for the hydrolysis of ester I 225 µl of each individual enzyme in 100 mM potassium phosphate buffer pH 7.5 was incubated with 2 mg of ester I dissolved in tert-butanol in a final volume of 250 µl in capped glass vials and incubated at 28° C. on an IKA KS 130 shaker (IKA, Staufen, Germany) at 400 rpm. After overnight incubation 40 µl 0.5 M phosphoric acid were added to each vial, subsequently diluted with 710 µl methyl-tert-butylether (MTBE) and centrifuged for 20 min at 3500 rpm in an Avanti J-20XPI centrifuge equipped with a JS-5.3 rotor (Beckman Coulter, Woerden, The Netherlands).
The enantiomeric excess (e.e.) of both the remaining ester as well as the resulting carboxylic acid was determined by HPLC (as described above). The conversion was calculated by comparison of these two c.c. values:

conversion=[e.e. ester/(e.e. ester+e.e. carboxylic acid)]*100%

Out of this large hydrolase collection only 8 recombinant pig liver esterases could hydrolyse preferentially the undesired enantiomer of ester I (Table 1).

TABLE 1 results of enzyme screening

| Esterase [SEQ ID No.] | e.e. ester I % | e.e. acid % | conversion % |
|---|---|---|---|
| 2 | 92.1 | 94 | 50 |
| 4 | 69.6 | 94 | 42 |
| 6 | 18.6 | 97 | 16 |
| 8 | 10.3 | 99 | 9 |
| 10 | 78.4 | 74 | 51 |
| 12 | 15.1 | 64 | 19 |

This example shows that several recombinant pig liver esterases hydrolyse ester I enantioselectively. Esterase enzymes showing the SEQ ID No.s 4, 6, 8, 10 or 12 can be prepared using *Escherichia coli* cells expressing the recombinant esterase genes of SEQ ID No.s 3, 5, 7, 9 or 11, respectively encoding said esterases according to the description in WO2009/004093 and WO2010/122175.

Example 6: Retest of Recombinant Pig Liver Esterases

Based on the results of the initial enzyme screening, 5 enzymes were selected for a retest at 250 mg scale. The selection of enzymes was based on activity and selectivity towards ester I. For each individual reaction 250 mg of ester I was dissolved in 1 ml tert-butanol. Subsequently 5 ml 100 mM potassium phosphate buffer pH 7.5 and 4 ml cell-free extract containing the respective overexpressed recombinant pig liver esterases were added in Metrohm 718 STAT Titrinos (Metrohm, Schiedam, The Netherlands) at enzyme/substrate ratios of 1 mg total protein per 1 mg ester I. The pH was kept constant at 7.5 with 1 M NaOH. At regular time points samples were analysed for the enantiomeric excess (e.e.) of both the remaining ester as well as the resulting carboxylic acid was determined by HPLC (as described above). The conversion was calculated by comparison of these two e.e. values. The results are given in Table 2.

TABLE 2

Conversion and e.e.s of pig liver esterases catalysed hydrolysis reaction of ester I to the corresponding carboxylic acid.

| | SEQ ID NO. 2 | | | SEQ ID NO. 4 | | |
|---|---|---|---|---|---|---|
| Time (h) | e.e. ester I (%) | e.e. acid (%) | conversion (%) | e.e. ester I (%) | e.e. acid (%) | conversion (%) |
| 1 | — | — | — | 2.6 | 80.3 | 3.1 |
| 2 | 32.5 | 99.9 | 24.5 | 3.9 | 90.0 | 4.1 |
| 3 | 50.7 | 99.7 | 33.7 | 5.7 | 91.8 | 5.9 |
| 5 | 99.5 | 99.6 | 50.0 | 8.3 | 92.0 | 8.3 |
| 7 | 99.3 | 99.9 | 49.9 | 14.1 | 91.6 | 13.3 |
| 23 | 99.9 | 99.9 | 50.0 | 27.6 | 92.4 | 23.0 |

TABLE 2-continued

Conversion and e.e.s of pig liver esterases catalysed hydrolysis reaction of ester I to the corresponding carboxylic acid.

| | SEQ ID NO. 6 | | | SEQ ID NO. 8 | | |
|---|---|---|---|---|---|---|
| Time (h) | e.e. ester I (%) | e.e. acid (%) | conversion (%) | e.e. ester I (%) | e.e. acid (%) | conversion (%) |
| 1 | −0.5 | 99.9 | 0.5 | 1.2 | 99.9 | 1.2 |
| 3 | 1.2 | 99.9 | 1.2 | 1.5 | 83.2 | 1.8 |
| 5 | 2.5 | 96.9 | 2.5 | 1.0 | 99.9 | 1.0 |
| 7 | 3.3 | 96.6 | 3.3 | 2.3 | 99.9 | 2.3 |
| 23 | 12.7 | 92.9 | 12.0 | 5.9 | 99.3 | 5.6 |

| | SEQ ID NO. 10 | | |
|---|---|---|---|
| Time (h) | e.e. ester I (%) | e.e. acid (%) | conversion (%) |
| 1 | 5.7 | 98.8 | 5.4 |
| 2 | 9.0 | 98.2 | 8.4 |
| 5 | 13.5 | 99.9 | 11.9 |
| 7 | 17.2 | 94.8 | 15.4 |

— = not determined

The enantioselectivities (E) of the individual esterase reaction were calculated from the conversion and the e.e. of the produced carboxylic acid according to the formula:

$$E = \ln((1-(\text{conversion}/100)*(1+(e.e._{acid}/100))))/\ln((1-(\text{conversion}/100)*(1-(e.e._{acid}/100))))$$

and given in Table 3.

TABLE 3

Enantioselectivity of the pig liver esterase catalysed hydrolysis of ester I

| Esterase [SEQ ID No.] | Enantioselectivity E |
|---|---|
| 2 | >500 |
| 4 | 30 |
| 6 | 30 |
| 8 | >200 |
| 10 | 45 |

The recombinant pig liver esterase of SEQ ID NO. 2 was identified as the best candidate with 50% conversion, an e.e of 99.5% for ester I after 5 h and an excellent enantioselectivity of E>500.

Example 7: Influence of Solvents on Pig Liver Esterase Reactions

The influence of organic solvents on the hydrolysis of ester I by the pig liver esterase of SEQ ID NO. 2 was investigated using recombinant *E. coli* cells expressing the gene of SEQ ID NO. 1, which had been produced as described in WO2010/122175. To 0.5 g of ester I 7.5 ml of 50 mM potassium phosphate buffer pH 7.8, 0.1 g of wet recombinant *E. coli* cells containing the esterase of SEQ ID NO. 1 (in 1 ml 50 mM potassium phosphate buffer pH 7.8) and 2.5 ml of organic solvent were added at 28° C. In separate reactions either toluene, methyl-isobutylketone, tert-butylacetate or 2-methyl-tetrahydrofurane were added as organic solvent. As control 2.5 ml of 50 mM potassium phosphate buffer pH 7.8 were added instead of an organic solvent.

The pH was kept constant at 7.8 with 1 M NaOH. At regular time points samples were analysed for the enantiomeric excess (e.e.) of both the remaining ester as well as the resulting carboxylic acid was determined by HPLC (as described above). The conversion was calculated by comparison of these two e.e. values (as described above). The results are given in table 4.

TABLE 4

Effect of organic solvents on the hydrolysis of R,R/S,S-Ester I by the recombinant pig liver esterase of SEQ ID No. 2.

| | time (h) | e.e acid (%) | e.e. ester I (%) | conversion (%) |
|---|---|---|---|---|
| no solvent | | | | |
| | 2 | 4.6 | 94 | 4.7 |
| | 3 | 6.8 | 98.3 | 6.5 |
| | 4 | 7.6 | 98.2 | 7.2 |
| | 7 | 12.2 | 97.1 | 11.2 |
| | 22 | 40.5 | 98.4 | 29.2 |
| toluene | | | | |
| | 2 | 10.1 | 98.0 | 9.3 |
| | 3 | 15.8 | 98.0 | 13.9 |
| | 4 | 21.7 | 98.0 | 18.1 |
| | 7 | 37.1 | 98.0 | 27.5 |
| | 22 | 99.3 | 99.2 | 50.0 |
| tert-butyl-acetate | | | | |
| | 2 | 5.0 | 95.6 | 5.0 |
| | 4 | 9.0 | 97.4 | 8.4 |
| | 6 | 15.1 | 97.9 | 13.4 |
| | 28.5 | 68.2 | 97.4 | 41.2 |
| methyl-isobutylketone | | | | |
| | 2 | 5.0 | 85.0 | 5.2 |
| | 7.5 | 5.3 | 95.0 | 5.6 |
| | 24 | 16.4 | 95.0 | 14.7 |

The solvents tert-butyl-acetate and especially toluene had a clear positive effect on the rate of ester I hydrolysis. With toluene ester I is obtained at 50.0% conversion and 99.2% e.e. after 22 hours.

The invention claimed is:

1. A mixture of 3-Hydroxy-2-methyl-4-[1,2,4]triazol-1-yl-3-phenyl-butyric acid ester diastereomers of formula (I):

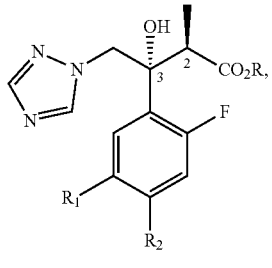

(2R, 3R)

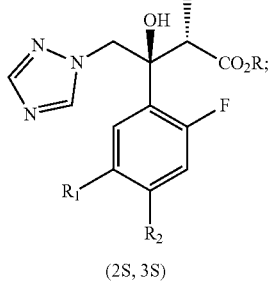

(2S, 3S)

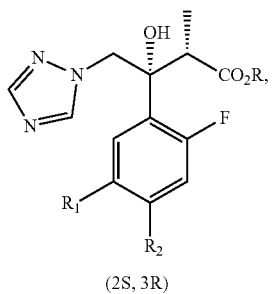

(2S, 3R)

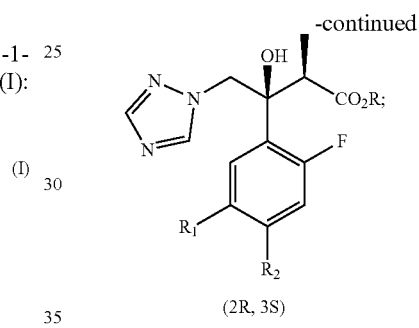

(2R, 3S)

comprising the racemic mixture of (2R,3R)/(2S,3S) esters at a diastereomeric excess, as determined by GC, between 97% and 99.9%, wherein $R_1$ is fluoro, $R_2$ is hydrogen and R is a $C_1$-$C_{12}$alkyl, a $C_5$-$C_{12}$aryl or a $C_6$-$C_{11}$aralkyl.

2. A (2R,3R)-3-Hydroxy-2-methyl-4-[1,2,4]triazol-1-yl-3-phenyl-butyric acid ester derivative according to formula (I):

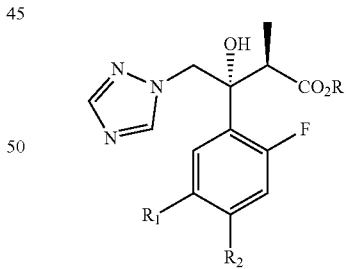

(R,R-Ester I)

wherein
R is a $C_1$-$C_{12}$ alkyl or $C_5$-$C_{12}$aryl,
$R_1$ is fluoro and
$R_2$ is hydrogen.

3. The mixture according to claim 1, wherein the racemic mixture of (2R,3R)/(2S,3S) esters at a diastereomeric excess, as determined by GC, is between 99% and 99.9%.

* * * * *

SEQUENCE LISTING

```
<160> NUMBER OF SEQ ID NOS: 12

<210> SEQ ID NO 1
<211> LENGTH: 1650
<212> TYPE: DNA
<213> ORGANISM: artificial sequence
<220> FEATURE:
<223> OTHER INFORMATION: gene PLE variant SEQ ID No. 2, codon optimized
<220> FEATURE:
<221> NAME/KEY: CDS
<222> LOCATION: (1)..(1650)
<223> OTHER INFORMATION: PLE variant
```

```
<400> SEQUENCE: 1 atg gga caa cca gct tcg ccg cct gtc gtt gat acc gct caa gga cga      48
Met Gly Gln Pro Ala Ser Pro Pro Val Val Asp Thr Ala Gln Gly Arg
1               5                   10                  15 gtc ttg ggt aag tac gtc tct tta gag gga ttg gca caa ccg gtt gct      96
Val Leu Gly Lys Tyr Val Ser Leu Glu Gly Leu Ala Gln Pro Val Ala
            20                  25                  30 gtc ttc ttg gga gtc cct ttt gct aag cca cct ctt gga tct ttg agg     144
Val Phe Leu Gly Val Pro Phe Ala Lys Pro Pro Leu Gly Ser Leu Arg
        35                  40                  45 ttt gcc ccg ccg caa cca gca gag cca tgg tct ttc gtt aag aac act     192
Phe Ala Pro Pro Gln Pro Ala Glu Pro Trp Ser Phe Val Lys Asn Thr
    50                  55                  60 act tcc tac cct cca atg tgt tgt caa gaa cca atc gga gga caa atg     240
Thr Ser Tyr Pro Pro Met Cys Cys Gln Glu Pro Ile Gly Gly Gln Met
65                  70                  75                  80 ctt tca gac cta ttc act aac aga aag gaa agg ctt atc ccg gag ttc     288
Leu Ser Asp Leu Phe Thr Asn Arg Lys Glu Arg Leu Ile Pro Glu Phe
                85                  90                  95 tct gag gat tgc ctt tac cta aat att tac act cct gcc gat ttg aca     336
Ser Glu Asp Cys Leu Tyr Leu Asn Ile Tyr Thr Pro Ala Asp Leu Thr
            100                 105                 110 aag agg ggt agg ttg ccg gtt atg gtt tgg att cat gga gga ggt ttg     384
Lys Arg Gly Arg Leu Pro Val Met Val Trp Ile His Gly Gly Gly Leu
        115                 120                 125 gtt gtt ggc gga gca tcc act tat gac gga ttg gct ctt gcc gcg cac     432
Val Val Gly Gly Ala Ser Thr Tyr Asp Gly Leu Ala Leu Ala Ala His
    130                 135                 140 gag aac gtt gtt gtt gtt gct att caa tac cgt ttg ggt att tgg gga     480
Glu Asn Val Val Val Val Ala Ile Gln Tyr Arg Leu Gly Ile Trp Gly
145                 150                 155                 160 ttt ttc tcc aca gga gat gag cat tcc cgt gga aac tgg ggc cat tta     528
Phe Phe Ser Thr Gly Asp Glu His Ser Arg Gly Asn Trp Gly His Leu
                165                 170                 175 gat caa gtt gct gca ttg cat tgg gtc caa gaa aac att gct aac ttc     576
Asp Gln Val Ala Ala Leu His Trp Val Gln Glu Asn Ile Ala Asn Phe
            180                 185                 190 gga ggt gat cca ggt tct gtt act att ttc gga gaa tca gca ggc gga     624
Gly Gly Asp Pro Gly Ser Val Thr Ile Phe Gly Glu Ser Ala Gly Gly
        195                 200                 205 gag agt gtc tct gta ttg gtt tta tca cca tta gct aag aac ctt ttt     672
Glu Ser Val Ser Val Leu Val Leu Ser Pro Leu Ala Lys Asn Leu Phe
    210                 215                 220 cat cgt gct att tcc gaa agt ggt gtt gct ttt acc gcc ggt gtg gtc     720
His Arg Ala Ile Ser Glu Ser Gly Val Ala Phe Thr Ala Gly Val Val
225                 230                 235                 240 agg aag gat atg aag gcc gca gcc aag cag atc gct gtc ctt gca gga     768
Arg Lys Asp Met Lys Ala Ala Ala Lys Gln Ile Ala Val Leu Ala Gly
                245                 250                 255 tgc aaa act act act tcg gca gtc ttc gtg cat tgt ttg cgt caa aag     816
Cys Lys Thr Thr Thr Ser Ala Val Phe Val His Cys Leu Arg Gln Lys
            260                 265                 270 tcg gaa gat gaa ctt tta gac ctc acg ttg aag atg aaa ttc ttt gcc     864
Ser Glu Asp Glu Leu Leu Asp Leu Thr Leu Lys Met Lys Phe Phe Ala
        275                 280                 285 ctt gac tta cac gga gat cca agg gaa tct cac cct ttt ttg acc act     912
Leu Asp Leu His Gly Asp Pro Arg Glu Ser His Pro Phe Leu Thr Thr
    290                 295                 300 gtt gtt gac gga gtt ttg ttg cct aag atg cct gag gaa atc ttg gcc     960
```

-continued

```
                Val Val Asp Gly Val Leu Leu Pro Lys Met Pro Glu Glu Ile Leu Ala
                305                 310                 315                 320 gag aag gac ttt aac acc gtc cca tac att gtt gga att aac aag cag          1008
Glu Lys Asp Phe Asn Thr Val Pro Tyr Ile Val Gly Ile Asn Lys Gln
                325                 330                 335 gag ttc gga tgg ctt ttg cca acg atg atg gga ttt cct ctt tcc gag          1056
Glu Phe Gly Trp Leu Leu Pro Thr Met Met Gly Phe Pro Leu Ser Glu
            340                 345                 350 gga aag ttg gat caa aag acg gct acg tca ctt ttg tgg aag tcc tac          1104
Gly Lys Leu Asp Gln Lys Thr Ala Thr Ser Leu Leu Trp Lys Ser Tyr
        355                 360                 365 cca att gcc aac att cct gaa gag ttg acc cca gtt gct acc gat aag          1152
Pro Ile Ala Asn Ile Pro Glu Glu Leu Thr Pro Val Ala Thr Asp Lys
    370                 375                 380 tat tta gga gga aca gat gat cct gtc aaa aag aaa gat ttg ttt ttg          1200
Tyr Leu Gly Gly Thr Asp Asp Pro Val Lys Lys Lys Asp Leu Phe Leu
385                 390                 395                 400 gat ctg atg gga gac gtt gtt ttc ggc gtc cca tca gtt acg gtt gct          1248
Asp Leu Met Gly Asp Val Val Phe Gly Val Pro Ser Val Thr Val Ala
                405                 410                 415 cgt cag cat agg gac gca gga gct cca act tac atg tat gag ttc caa          1296
Arg Gln His Arg Asp Ala Gly Ala Pro Thr Tyr Met Tyr Glu Phe Gln
            420                 425                 430 tat cgt cca tct ttt tca tcg gat aag aaa cct aag acg gtt att gga          1344
Tyr Arg Pro Ser Phe Ser Ser Asp Lys Lys Pro Lys Thr Val Ile Gly
        435                 440                 445 gat cat gga gac gaa att ttt tcc gtc ttc ggc ttc cca ttg ctc aaa          1392
Asp His Gly Asp Glu Ile Phe Ser Val Phe Gly Phe Pro Leu Leu Lys
    450                 455                 460 ggt gac gct cca gag gaa gaa gtc agt ctt tct aag acg gtt atg aaa          1440
Gly Asp Ala Pro Glu Glu Glu Val Ser Leu Ser Lys Thr Val Met Lys
465                 470                 475                 480 ttt tgg gct aac ttc gcc cgt agt gga aac cct aat gga gaa gga ttg          1488
Phe Trp Ala Asn Phe Ala Arg Ser Gly Asn Pro Asn Gly Glu Gly Leu
                485                 490                 495 cct cac tgg ccg atg tac gat caa gag gag gga tac ctt caa att ggt          1536
Pro His Trp Pro Met Tyr Asp Gln Glu Glu Gly Tyr Leu Gln Ile Gly
            500                 505                 510 gtc aac act caa gca gct aag agg ttg aaa ggc gag gag gtt gct ttt          1584
Val Asn Thr Gln Ala Ala Lys Arg Leu Lys Gly Glu Glu Val Ala Phe
        515                 520                 525 tgg aac gac ctg ttg tcc aag gaa gca gca aag aag cca cct aag ata          1632
Trp Asn Asp Leu Leu Ser Lys Glu Ala Ala Lys Lys Pro Pro Lys Ile
    530                 535                 540 aag cac gcc gaa ttg taa                                                  1650
Lys His Ala Glu Leu
545

<210> SEQ ID NO 2
<211> LENGTH: 549
<212> TYPE: PRT
<213> ORGANISM: artificial sequence
<220> FEATURE:
<223> OTHER INFORMATION: Synthetic Construct

<400> SEQUENCE: 2

Met Gly Gln Pro Ala Ser Pro Val Val Asp Thr Ala Gln Gly Arg
1               5                   10                  15

Val Leu Gly Lys Tyr Val Ser Leu Glu Gly Leu Ala Gln Pro Val Ala
                20                  25                  30
```

-continued

```
Val Phe Leu Gly Val Pro Phe Ala Lys Pro Pro Leu Gly Ser Leu Arg
         35                  40                  45

Phe Ala Pro Pro Gln Pro Ala Glu Pro Trp Ser Phe Val Lys Asn Thr
 50                  55                  60

Thr Ser Tyr Pro Pro Met Cys Cys Gln Glu Pro Ile Gly Gly Gln Met
 65                  70                  75                  80

Leu Ser Asp Leu Phe Thr Asn Arg Lys Glu Arg Leu Ile Pro Glu Phe
                 85                  90                  95

Ser Glu Asp Cys Leu Tyr Leu Asn Ile Tyr Thr Pro Ala Asp Leu Thr
             100                 105                 110

Lys Arg Gly Arg Leu Pro Val Met Val Trp Ile His Gly Gly Gly Leu
         115                 120                 125

Val Val Gly Gly Ala Ser Thr Tyr Asp Gly Leu Ala Leu Ala Ala His
     130                 135                 140

Glu Asn Val Val Val Ala Ile Gln Tyr Arg Leu Gly Ile Trp Gly
145                 150                 155                 160

Phe Phe Ser Thr Gly Asp Glu His Ser Arg Gly Asn Trp Gly His Leu
                 165                 170                 175

Asp Gln Val Ala Ala Leu His Trp Val Gln Glu Asn Ile Ala Asn Phe
             180                 185                 190

Gly Gly Asp Pro Gly Ser Val Thr Ile Phe Gly Glu Ser Ala Gly Gly
         195                 200                 205

Glu Ser Val Ser Val Leu Val Leu Ser Pro Leu Ala Lys Asn Leu Phe
     210                 215                 220

His Arg Ala Ile Ser Glu Ser Gly Val Ala Phe Thr Ala Gly Val Val
225                 230                 235                 240

Arg Lys Asp Met Lys Ala Ala Lys Gln Ile Ala Val Leu Ala Gly
                 245                 250                 255

Cys Lys Thr Thr Thr Ser Ala Val Phe Val His Cys Leu Arg Gln Lys
             260                 265                 270

Ser Glu Asp Glu Leu Leu Asp Leu Thr Leu Lys Met Lys Phe Phe Ala
         275                 280                 285

Leu Asp Leu His Gly Asp Pro Arg Glu Ser His Pro Phe Leu Thr Thr
     290                 295                 300

Val Val Asp Gly Val Leu Leu Pro Lys Met Pro Glu Glu Ile Leu Ala
305                 310                 315                 320

Glu Lys Asp Phe Asn Thr Val Pro Tyr Ile Val Gly Ile Asn Lys Gln
                 325                 330                 335

Glu Phe Gly Trp Leu Leu Pro Thr Met Met Gly Phe Pro Leu Ser Glu
             340                 345                 350

Gly Lys Leu Asp Gln Lys Thr Ala Thr Ser Leu Leu Trp Lys Ser Tyr
         355                 360                 365

Pro Ile Ala Asn Ile Pro Glu Glu Leu Thr Pro Val Ala Thr Asp Lys
     370                 375                 380

Tyr Leu Gly Gly Thr Asp Asp Pro Val Lys Lys Lys Asp Leu Phe Leu
385                 390                 395                 400

Asp Leu Met Gly Asp Val Val Phe Gly Val Pro Ser Val Thr Val Ala
                 405                 410                 415

Arg Gln His Arg Asp Ala Gly Ala Pro Thr Tyr Met Tyr Glu Phe Gln
             420                 425                 430

Tyr Arg Pro Ser Phe Ser Ser Asp Lys Lys Pro Lys Thr Val Ile Gly
         435                 440                 445

Asp His Gly Asp Glu Ile Phe Ser Val Phe Gly Phe Pro Leu Leu Lys
```

```
                450              455              460
Gly Asp Ala Pro Glu Glu Val Ser Leu Ser Lys Thr Val Met Lys
465             470                  475                 480

Phe Trp Ala Asn Phe Ala Arg Ser Gly Asn Pro Asn Gly Glu Gly Leu
                    485                 490                 495

Pro His Trp Pro Met Tyr Asp Gln Glu Gly Tyr Leu Gln Ile Gly
                500                 505                 510

Val Asn Thr Gln Ala Ala Lys Arg Leu Lys Gly Glu Glu Val Ala Phe
            515                 520                 525

Trp Asn Asp Leu Leu Ser Lys Glu Ala Ala Lys Lys Pro Pro Lys Ile
    530                 535                 540

Lys His Ala Glu Leu
545

<210> SEQ ID NO 3
<211> LENGTH: 1650
<212> TYPE: DNA
<213> ORGANISM: artificial sequence
<220> FEATURE:
<223> OTHER INFORMATION: gene APLE SEQ ID No. 4, codon optimized
<220> FEATURE:
<221> NAME/KEY: CDS
<222> LOCATION: (1)..(1650)
<223> OTHER INFORMATION: APLE

<400> SEQUENCE: 3 atg gga caa cca gct tcg ccg cct gtc gtt gat acc gct caa gga cga      48
Met Gly Gln Pro Ala Ser Pro Pro Val Val Asp Thr Ala Gln Gly Arg
1               5                   10                  15 gtc ttg ggt aag tac gtc tct tta gag gga ttg gca caa ccg gtt gct      96
Val Leu Gly Lys Tyr Val Ser Leu Glu Gly Leu Ala Gln Pro Val Ala
            20                  25                  30 gtc ttc ttg gga gtc cct ttt gct aag cca cct ctt gga tct ttg agg     144
Val Phe Leu Gly Val Pro Phe Ala Lys Pro Pro Leu Gly Ser Leu Arg
        35                  40                  45 ttt gcc ccg ccg caa cca gca gag cca tgg tct ttc gtt aag aac act     192
Phe Ala Pro Pro Gln Pro Ala Glu Pro Trp Ser Phe Val Lys Asn Thr
    50                  55                  60 act tcc tac cct cca atg tgt tgt caa gaa cca atc gga gga caa atg     240
Thr Ser Tyr Pro Pro Met Cys Cys Gln Glu Pro Ile Gly Gly Gln Met
65                  70                  75                  80 ctt tca gac cta ttc act aac aga aag gaa agg ctt atc ccg gag ttc     288
Leu Ser Asp Leu Phe Thr Asn Arg Lys Glu Arg Leu Ile Pro Glu Phe
                85                  90                  95 tct gag gat tgc ctt tac cta aat att tac act cct gcc gat ttg aca     336
Ser Glu Asp Cys Leu Tyr Leu Asn Ile Tyr Thr Pro Ala Asp Leu Thr
            100                 105                 110 aag agg ggt agg ttg ccg gtt atg gtt tgg att cat gga gga ggt ttg     384
Lys Arg Gly Arg Leu Pro Val Met Val Trp Ile His Gly Gly Gly Leu
        115                 120                 125 gtt gtt ggc gga gca tcc act tat gac gga ttg gct ctt gcc gcg cac     432
Val Val Gly Gly Ala Ser Thr Tyr Asp Gly Leu Ala Leu Ala Ala His
    130                 135                 140 gag aac gtt gtt gtt gtt gct att caa tac cgt ttg ggt att tgg gga     480
Glu Asn Val Val Val Val Ala Ile Gln Tyr Arg Leu Gly Ile Trp Gly
145                 150                 155                 160 ttt ttc tcc aca gga gat gag cat tcc cgt gga aac tgg ggc cat tta     528
Phe Phe Ser Thr Gly Asp Glu His Ser Arg Gly Asn Trp Gly His Leu
                165                 170                 175 gat caa gtt gct gca ttg cat tgg gtc caa gaa aac att gct aac ttc     576
```

```
                Asp Gln Val Ala Ala Leu His Trp Val Gln Glu Asn Ile Ala Asn Phe
                            180                 185                 190 gga ggt gat cca ggt tct gtt act att ttc gga gaa tca gca ggc gga        624
Gly Gly Asp Pro Gly Ser Val Thr Ile Phe Gly Glu Ser Ala Gly Gly
            195                 200                 205 gag agt gtc tct gta ttg gtt tta tca cca tta gct aag aac ctt ttt        672
Glu Ser Val Ser Val Leu Val Leu Ser Pro Leu Ala Lys Asn Leu Phe
210                 215                 220 cat cgt gct att tcc gaa agt ggt gtt gct ttt acc gcc ggt ttg gtc        720
His Arg Ala Ile Ser Glu Ser Gly Val Ala Phe Thr Ala Gly Leu Val
225                 230                 235                 240 agg aag gat atg aag gcc gca gcc aag cag atc gct gtc ctt gca gga        768
Arg Lys Asp Met Lys Ala Ala Ala Lys Gln Ile Ala Val Leu Ala Gly
            245                 250                 255 tgc aaa act act act tcg gca gtc ttc gtg cat tgt ttg cgt caa aag        816
Cys Lys Thr Thr Thr Ser Ala Val Phe Val His Cys Leu Arg Gln Lys
            260                 265                 270 tcg gaa gat gaa ctt tta gac ctc acg ttg aag atg aaa ttc ttt gcc        864
Ser Glu Asp Glu Leu Leu Asp Leu Thr Leu Lys Met Lys Phe Phe Ala
            275                 280                 285 ctt gac tta cac gga gat cca agg gaa tct cac cct ttt ttg acc act        912
Leu Asp Leu His Gly Asp Pro Arg Glu Ser His Pro Phe Leu Thr Thr
            290                 295                 300 gtt gtt gac gga gtt ttg ttg cct aag atg cct gag gaa atc ttg gcc        960
Val Val Asp Gly Val Leu Leu Pro Lys Met Pro Glu Glu Ile Leu Ala
305                 310                 315                 320 gag aag gac ttt aac acc gtc cca tac att gtt gga att aac aag cag       1008
Glu Lys Asp Phe Asn Thr Val Pro Tyr Ile Val Gly Ile Asn Lys Gln
                325                 330                 335 gag ttc gga tgg ctt ttg cca acg atg atg gga ttt cct ctt tcc gag       1056
Glu Phe Gly Trp Leu Leu Pro Thr Met Met Gly Phe Pro Leu Ser Glu
            340                 345                 350 gga aag ttg gat caa aag acg gct acg tca ctt ttg tgg aag tcc tac       1104
Gly Lys Leu Asp Gln Lys Thr Ala Thr Ser Leu Leu Trp Lys Ser Tyr
            355                 360                 365 cca att gcc aac att cct gaa gag ttg acc cca gtt gct acc gat aag       1152
Pro Ile Ala Asn Ile Pro Glu Glu Leu Thr Pro Val Ala Thr Asp Lys
370                 375                 380 tat tta gga gga aca gat gat cct gtc aaa aag aaa gat ttg ttt ttg       1200
Tyr Leu Gly Gly Thr Asp Asp Pro Val Lys Lys Lys Asp Leu Phe Leu
385                 390                 395                 400 gat ctg atg gga gac gtt gtt ttc ggc gtc cca tca gtt acg gtt gct       1248
Asp Leu Met Gly Asp Val Val Phe Gly Val Pro Ser Val Thr Val Ala
                405                 410                 415 cgt cag cat agg gac gca gga gct cca act tac atg tat gag ttc caa       1296
Arg Gln His Arg Asp Ala Gly Ala Pro Thr Tyr Met Tyr Glu Phe Gln
            420                 425                 430 tat cgt cca tct ttt tca tcg gat aag aaa cct aag acg gtt att gga       1344
Tyr Arg Pro Ser Phe Ser Ser Asp Lys Lys Pro Lys Thr Val Ile Gly
            435                 440                 445 gat cat gga gac gaa att ttt tcc gtc ttc ggc ttc cca ttg ctc aaa       1392
Asp His Gly Asp Glu Ile Phe Ser Val Phe Gly Phe Pro Leu Leu Lys
450                 455                 460 ggt gac gct cca gag gaa gaa gtc agt ctt tct aag acg gtt atg aaa       1440
Gly Asp Ala Pro Glu Glu Glu Val Ser Leu Ser Lys Thr Val Met Lys
465                 470                 475                 480 ttt tgg gct aac ttc gcc cgt agt gga aac cct aat gga gaa gga ttg       1488
Phe Trp Ala Asn Phe Ala Arg Ser Gly Asn Pro Asn Gly Glu Gly Leu
                485                 490                 495
```

```
cct cac tgg ccg atg tac gat caa gag gag gga tac ctt caa att ggt    1536
Pro His Trp Pro Met Tyr Asp Gln Glu Glu Gly Tyr Leu Gln Ile Gly
            500                 505                 510 gtc aac act caa gca gct aag agg ttg aaa ggc gag gag gtt gct ttt    1584
Val Asn Thr Gln Ala Ala Lys Arg Leu Lys Gly Glu Glu Val Ala Phe
            515                 520                 525 tgg aac gac ctg ttg tcc aag gaa gca gca aag aag cca cct aag ata    1632
Trp Asn Asp Leu Leu Ser Lys Glu Ala Ala Lys Lys Pro Pro Lys Ile
530                 535                 540 aag cac gcc gaa ttg taa                                            1650
Lys His Ala Glu Leu
545
```

<210> SEQ ID NO 4
<211> LENGTH: 549
<212> TYPE: PRT
<213> ORGANISM: artificial sequence
<220> FEATURE:
<223> OTHER INFORMATION: Synthetic Construct

<400> SEQUENCE: 4

```
Met Gly Gln Pro Ala Ser Pro Pro Val Val Asp Thr Ala Gln Gly Arg
1               5                   10                  15

Val Leu Gly Lys Tyr Val Ser Leu Glu Gly Leu Ala Gln Pro Val Ala
            20                  25                  30

Val Phe Leu Gly Val Pro Phe Ala Lys Pro Pro Leu Gly Ser Leu Arg
        35                  40                  45

Phe Ala Pro Pro Gln Pro Ala Glu Pro Trp Ser Phe Val Lys Asn Thr
    50                  55                  60

Thr Ser Tyr Pro Pro Met Cys Cys Gln Glu Pro Ile Gly Gly Gln Met
65                  70                  75                  80

Leu Ser Asp Leu Phe Thr Asn Arg Lys Glu Arg Leu Ile Pro Glu Phe
                85                  90                  95

Ser Glu Asp Cys Leu Tyr Leu Asn Ile Tyr Thr Pro Ala Asp Leu Thr
            100                 105                 110

Lys Arg Gly Arg Leu Pro Val Met Val Trp Ile His Gly Gly Gly Leu
        115                 120                 125

Val Val Gly Gly Ala Ser Thr Tyr Asp Gly Leu Ala Leu Ala Ala His
    130                 135                 140

Glu Asn Val Val Val Ala Ile Gln Tyr Arg Leu Gly Ile Trp Gly
145                 150                 155                 160

Phe Phe Ser Thr Gly Asp Glu His Ser Arg Gly Asn Trp Gly His Leu
                165                 170                 175

Asp Gln Val Ala Ala Leu His Trp Val Gln Glu Asn Ile Ala Asn Phe
            180                 185                 190

Gly Gly Asp Pro Gly Ser Val Thr Ile Phe Gly Glu Ser Ala Gly Gly
        195                 200                 205

Glu Ser Val Ser Val Leu Val Leu Ser Pro Leu Ala Lys Asn Leu Phe
    210                 215                 220

His Arg Ala Ile Ser Glu Ser Gly Val Ala Phe Thr Ala Gly Leu Val
225                 230                 235                 240

Arg Lys Asp Met Lys Ala Ala Lys Gln Ile Ala Val Leu Ala Gly
                245                 250                 255

Cys Lys Thr Thr Thr Ser Ala Val Phe Val His Cys Leu Arg Gln Lys
            260                 265                 270

Ser Glu Asp Glu Leu Leu Asp Leu Thr Leu Lys Met Lys Phe Phe Ala
        275                 280                 285
```

```
Leu Asp Leu His Gly Asp Pro Arg Glu Ser His Pro Phe Leu Thr Thr
    290                 295                 300

Val Val Asp Gly Val Leu Leu Pro Lys Met Pro Glu Glu Ile Leu Ala
305                 310                 315                 320

Glu Lys Asp Phe Asn Thr Val Pro Tyr Ile Val Gly Ile Asn Lys Gln
                    325                 330                 335

Glu Phe Gly Trp Leu Leu Pro Thr Met Met Gly Phe Pro Leu Ser Glu
                340                 345                 350

Gly Lys Leu Asp Gln Lys Thr Ala Thr Ser Leu Leu Trp Lys Ser Tyr
            355                 360                 365

Pro Ile Ala Asn Ile Pro Glu Glu Leu Thr Pro Val Ala Thr Asp Lys
        370                 375                 380

Tyr Leu Gly Gly Thr Asp Asp Pro Val Lys Lys Lys Asp Leu Phe Leu
385                 390                 395                 400

Asp Leu Met Gly Asp Val Val Phe Gly Val Pro Ser Val Thr Val Ala
                405                 410                 415

Arg Gln His Arg Asp Ala Gly Ala Pro Thr Tyr Met Tyr Glu Phe Gln
                    420                 425                 430

Tyr Arg Pro Ser Phe Ser Ser Asp Lys Lys Pro Lys Thr Val Ile Gly
                435                 440                 445

Asp His Gly Asp Glu Ile Phe Ser Val Phe Gly Phe Pro Leu Leu Lys
            450                 455                 460

Gly Asp Ala Pro Glu Glu Glu Val Ser Leu Ser Lys Thr Val Met Lys
465                 470                 475                 480

Phe Trp Ala Asn Phe Ala Arg Ser Gly Asn Pro Asn Gly Glu Gly Leu
                    485                 490                 495

Pro His Trp Pro Met Tyr Asp Gln Glu Glu Gly Tyr Leu Gln Ile Gly
                500                 505                 510

Val Asn Thr Gln Ala Ala Lys Arg Leu Lys Gly Glu Glu Val Ala Phe
            515                 520                 525

Trp Asn Asp Leu Leu Ser Lys Glu Ala Ala Lys Lys Pro Pro Lys Ile
        530                 535                 540

Lys His Ala Glu Leu
545

<210> SEQ ID NO 5
<211> LENGTH: 1650
<212> TYPE: DNA
<213> ORGANISM: artificial sequence
<220> FEATURE:
<223> OTHER INFORMATION: gene APLE Hybrid 3 SEQ ID No. 6, codon
      optimized
<220> FEATURE:
<221> NAME/KEY: CDS
<222> LOCATION: (1)..(1650)
<223> OTHER INFORMATION: APLE Hybrid 3

<400> SEQUENCE: 5 atg gga caa cca gct tcg ccg cct gtc gtt gat acc gct caa gga cga    48
Met Gly Gln Pro Ala Ser Pro Pro Val Val Asp Thr Ala Gln Gly Arg
1               5                   10                  15 gtc ttg ggt aag tac gtc tct tta gag gga ttg gca caa ccg gtt gct    96
Val Leu Gly Lys Tyr Val Ser Leu Glu Gly Leu Ala Gln Pro Val Ala
            20                  25                  30 gtc ttc ttg gga gtc cct ttt gct aag cca cct ctt gga tct ttg agg   144
Val Phe Leu Gly Val Pro Phe Ala Lys Pro Pro Leu Gly Ser Leu Arg
        35                  40                  45
```

| | | |
|---|---|---|
| ttt gcc ccg ccg caa cca gca gag cca tgg tct ttc gtt aag aac act<br>Phe Ala Pro Pro Gln Pro Ala Glu Pro Trp Ser Phe Val Lys Asn Thr<br>50 55 60 | | 192 |
| act tcc tac cct cca atg tgt tgt caa gaa cca atc gga gga caa atg<br>Thr Ser Tyr Pro Pro Met Cys Cys Gln Glu Pro Ile Gly Gly Gln Met<br>65 70 75 80 | | 240 |
| ctt tca gac cta ttc act aac aga aag gaa agg ctt atc ccg gag ttc<br>Leu Ser Asp Leu Phe Thr Asn Arg Lys Glu Arg Leu Ile Pro Glu Phe<br>85 90 95 | | 288 |
| tct gag gat tgc ctt tac cta aat att tac act cct gcc gat ttg aca<br>Ser Glu Asp Cys Leu Tyr Leu Asn Ile Tyr Thr Pro Ala Asp Leu Thr<br>100 105 110 | | 336 |
| aag agg ggt agg ttg ccg gtt atg gtt tgg att cat gga gga ggt ttg<br>Lys Arg Gly Arg Leu Pro Val Met Val Trp Ile His Gly Gly Gly Leu<br>115 120 125 | | 384 |
| gtt gtt ggc gga gca tcc act tat gac gga ttg gct ctt gcc gcg cac<br>Val Val Gly Gly Ala Ser Thr Tyr Asp Gly Leu Ala Leu Ala Ala His<br>130 135 140 | | 432 |
| gag aac gtt gtt gtt gtt gct att caa tac cgt ttg ggt att tgg gga<br>Glu Asn Val Val Val Val Ala Ile Gln Tyr Arg Leu Gly Ile Trp Gly<br>145 150 155 160 | | 480 |
| ttt ttc tcc aca gga gat gag cat tcc cgt gga aac tgg ggc cat tta<br>Phe Phe Ser Thr Gly Asp Glu His Ser Arg Gly Asn Trp Gly His Leu<br>165 170 175 | | 528 |
| gat caa gtt gct gca ttg cat tgg gtc caa gaa aac att gct aac ttc<br>Asp Gln Val Ala Ala Leu His Trp Val Gln Glu Asn Ile Ala Asn Phe<br>180 185 190 | | 576 |
| gga ggt gat cca ggt tct gtt act att ttc gga gaa tca gca ggc gga<br>Gly Gly Asp Pro Gly Ser Val Thr Ile Phe Gly Glu Ser Ala Gly Gly<br>195 200 205 | | 624 |
| gag agt gtc tct gta ttg gtt tta tca cca tta gct aag aac ctt ttt<br>Glu Ser Val Ser Val Leu Val Leu Ser Pro Leu Ala Lys Asn Leu Phe<br>210 215 220 | | 672 |
| cat cgt gct att tcc gaa agt ggt gtt gct tta acc gtc gct ttg gtc<br>His Arg Ala Ile Ser Glu Ser Gly Val Ala Leu Thr Val Ala Leu Val<br>225 230 235 240 | | 720 |
| agg aag gat atg aag gcc gca gcc aag cag atc gct gtc ctt gca gga<br>Arg Lys Asp Met Lys Ala Ala Ala Lys Gln Ile Ala Val Leu Ala Gly<br>245 250 255 | | 768 |
| tgc aaa act act act tcg gca gtc ttc gtg cat tgt ttg cgt caa aag<br>Cys Lys Thr Thr Thr Ser Ala Val Phe Val His Cys Leu Arg Gln Lys<br>260 265 270 | | 816 |
| tcg gaa gat gaa ctt tta gac ctc acg ttg aag atg aaa ttc ttt gcc<br>Ser Glu Asp Glu Leu Leu Asp Leu Thr Leu Lys Met Lys Phe Phe Ala<br>275 280 285 | | 864 |
| ctt gac tta cac gga gat cca agg gaa tct cac cct ttt ttg acc act<br>Leu Asp Leu His Gly Asp Pro Arg Glu Ser His Pro Phe Leu Thr Thr<br>290 295 300 | | 912 |
| gtt gtt gac gga gtt ttg ttg cct aag atg cct gag gaa atc ttg gcc<br>Val Val Asp Gly Val Leu Leu Pro Lys Met Pro Glu Glu Ile Leu Ala<br>305 310 315 320 | | 960 |
| gag aag gac ttt aac acc gtc cca tac att gtt gga att aac aag cag<br>Glu Lys Asp Phe Asn Thr Val Pro Tyr Ile Val Gly Ile Asn Lys Gln<br>325 330 335 | | 1008 |
| gag ttc gga tgg ctt ttg cca acg atg atg gga ttt cct ctt tcc gag<br>Glu Phe Gly Trp Leu Leu Pro Thr Met Met Gly Phe Pro Leu Ser Glu<br>340 345 350 | | 1056 |
| gga aag ttg gat caa aag acg gct acg tca ctt ttg tgg aag tcc tac<br>Gly Lys Leu Asp Gln Lys Thr Ala Thr Ser Leu Leu Trp Lys Ser Tyr<br>355 360 365 | | 1104 |

-continued

```
cca att gcc aac att cct gaa gag ttg acc cca gtt gct acc gat aag      1152
Pro Ile Ala Asn Ile Pro Glu Glu Leu Thr Pro Val Ala Thr Asp Lys
    370                 375                 380 tat tta gga gga aca gat gat cct gtc aaa aag aaa gat ttg ttt ttg      1200
Tyr Leu Gly Gly Thr Asp Asp Pro Val Lys Lys Lys Asp Leu Phe Leu
385                 390                 395                 400 gat ctg atg gga gac gtt gtt ttc ggc gtc cca tca gtt acg gtt gct      1248
Asp Leu Met Gly Asp Val Val Phe Gly Val Pro Ser Val Thr Val Ala
                405                 410                 415 cgt cag cat agg gac gca gga gct cca act tac atg tat gag ttc caa      1296
Arg Gln His Arg Asp Ala Gly Ala Pro Thr Tyr Met Tyr Glu Phe Gln
            420                 425                 430 tat cgt cca tct ttt tca tcg gat aag aaa cct aag acg gtt att gga      1344
Tyr Arg Pro Ser Phe Ser Ser Asp Lys Lys Pro Lys Thr Val Ile Gly
        435                 440                 445 gat cat gga gac gaa att ttt tcc gtc ttc ggc ttc cca ttg ctc aaa      1392
Asp His Gly Asp Glu Ile Phe Ser Val Phe Gly Phe Pro Leu Leu Lys
    450                 455                 460 ggt gac gct cca gag gaa gaa gtc agt ctt tct aag acg gtt atg aaa      1440
Gly Asp Ala Pro Glu Glu Glu Val Ser Leu Ser Lys Thr Val Met Lys
465                 470                 475                 480 ttt tgg gct aac ttc gcc cgt agt gga aac cct aat gga gaa gga ttg      1488
Phe Trp Ala Asn Phe Ala Arg Ser Gly Asn Pro Asn Gly Glu Gly Leu
                485                 490                 495 cct cac tgg ccg atg tac gat caa gag gag gga tac ctt caa att ggt      1536
Pro His Trp Pro Met Tyr Asp Gln Glu Glu Gly Tyr Leu Gln Ile Gly
            500                 505                 510 gtc aac act caa gca gct aag agg ttg aaa ggc gag gag gtt gct ttt      1584
Val Asn Thr Gln Ala Ala Lys Arg Leu Lys Gly Glu Glu Val Ala Phe
        515                 520                 525 tgg aac gac ctg ttg tcc aag gaa gca gca aag aag cca cct aag ata      1632
Trp Asn Asp Leu Leu Ser Lys Glu Ala Ala Lys Lys Pro Pro Lys Ile
    530                 535                 540 aag cac gcc gaa ttg taa                                              1650
Lys His Ala Glu Leu
545
```

<210> SEQ ID NO 6
<211> LENGTH: 549
<212> TYPE: PRT
<213> ORGANISM: artificial sequence
<220> FEATURE:
<223> OTHER INFORMATION: Synthetic Construct

<400> SEQUENCE: 6

```
Met Gly Gln Pro Ala Ser Pro Pro Val Val Asp Thr Ala Gln Gly Arg
1               5                   10                  15

Val Leu Gly Lys Tyr Val Ser Leu Glu Gly Leu Ala Gln Pro Val Ala
                20                  25                  30

Val Phe Leu Gly Val Pro Phe Ala Lys Pro Pro Leu Gly Ser Leu Arg
            35                  40                  45

Phe Ala Pro Pro Gln Pro Ala Glu Pro Trp Ser Phe Val Lys Asn Thr
        50                  55                  60

Thr Ser Tyr Pro Pro Met Cys Cys Gln Glu Pro Ile Gly Gly Gln Met
65                  70                  75                  80

Leu Ser Asp Leu Phe Thr Asn Arg Lys Glu Arg Leu Ile Pro Glu Phe
                85                  90                  95

Ser Glu Asp Cys Leu Tyr Leu Asn Ile Tyr Thr Pro Ala Asp Leu Thr
            100                 105                 110
```

-continued

Lys Arg Gly Arg Leu Pro Val Met Val Trp Ile His Gly Gly Leu
        115                 120                 125
Val Val Gly Gly Ala Ser Thr Tyr Asp Gly Leu Ala Leu Ala Ala His
130                 135                 140
Glu Asn Val Val Val Ala Ile Gln Tyr Arg Leu Gly Ile Trp Gly
145                 150                 155                 160
Phe Phe Ser Thr Gly Asp Glu His Ser Arg Gly Asn Trp Gly His Leu
                165                 170                 175
Asp Gln Val Ala Ala Leu His Trp Val Gln Glu Asn Ile Ala Asn Phe
            180                 185                 190
Gly Gly Asp Pro Gly Ser Val Thr Ile Phe Gly Glu Ser Ala Gly Gly
        195                 200                 205
Glu Ser Val Ser Val Leu Val Leu Ser Pro Leu Ala Lys Asn Leu Phe
210                 215                 220
His Arg Ala Ile Ser Glu Ser Gly Val Ala Leu Thr Val Ala Leu Val
225                 230                 235                 240
Arg Lys Asp Met Lys Ala Ala Ala Lys Gln Ile Ala Val Leu Ala Gly
                245                 250                 255
Cys Lys Thr Thr Thr Ser Ala Val Phe Val His Cys Leu Arg Gln Lys
            260                 265                 270
Ser Glu Asp Glu Leu Leu Asp Leu Thr Leu Lys Met Lys Phe Phe Ala
        275                 280                 285
Leu Asp Leu His Gly Asp Pro Arg Glu Ser His Pro Phe Leu Thr Thr
    290                 295                 300
Val Val Asp Gly Val Leu Leu Pro Lys Met Pro Glu Glu Ile Leu Ala
305                 310                 315                 320
Glu Lys Asp Phe Asn Thr Val Pro Tyr Ile Val Gly Ile Asn Lys Gln
                325                 330                 335
Glu Phe Gly Trp Leu Leu Pro Thr Met Met Gly Phe Pro Leu Ser Glu
            340                 345                 350
Gly Lys Leu Asp Gln Lys Thr Ala Thr Ser Leu Leu Trp Lys Ser Tyr
        355                 360                 365
Pro Ile Ala Asn Ile Pro Glu Glu Leu Thr Pro Val Ala Thr Asp Lys
    370                 375                 380
Tyr Leu Gly Gly Thr Asp Asp Pro Val Lys Lys Lys Asp Leu Phe Leu
385                 390                 395                 400
Asp Leu Met Gly Asp Val Val Phe Gly Val Pro Ser Val Thr Val Ala
                405                 410                 415
Arg Gln His Arg Asp Ala Gly Ala Pro Thr Tyr Met Tyr Glu Phe Gln
            420                 425                 430
Tyr Arg Pro Ser Phe Ser Ser Asp Lys Lys Pro Lys Thr Val Ile Gly
        435                 440                 445
Asp His Gly Asp Glu Ile Phe Ser Val Phe Gly Phe Pro Leu Leu Lys
    450                 455                 460
Gly Asp Ala Pro Glu Glu Val Ser Leu Ser Lys Thr Val Met Lys
465                 470                 475                 480
Phe Trp Ala Asn Phe Ala Arg Ser Gly Asn Pro Asn Gly Glu Gly Leu
                485                 490                 495
Pro His Trp Pro Met Tyr Asp Gln Glu Glu Gly Tyr Leu Gln Ile Gly
            500                 505                 510
Val Asn Thr Gln Ala Ala Lys Arg Leu Lys Gly Glu Glu Val Ala Phe
        515                 520                 525

```
Trp Asn Asp Leu Leu Ser Lys Glu Ala Ala Lys Lys Pro Pro Lys Ile
        530                 535                 540

Lys His Ala Glu Leu
545

<210> SEQ ID NO 7
<211> LENGTH: 1650
<212> TYPE: DNA
<213> ORGANISM: artificial sequence
<220> FEATURE:
<223> OTHER INFORMATION: gene APLE Hybrid 1 SEQ ID No. 8
<220> FEATURE:
<221> NAME/KEY: CDS
<222> LOCATION: (1)..(1650)
<223> OTHER INFORMATION: APLE Hybrid 1

<400> SEQUENCE: 7 atg gga caa cca gct tcg ccg cct gtc gtt gat acc gct caa gga cga      48
Met Gly Gln Pro Ala Ser Pro Pro Val Val Asp Thr Ala Gln Gly Arg
1               5                  10                  15 gtc ttg ggt aag tac gtc tct tta gag gga ttg gca caa ccg gtt gct      96
Val Leu Gly Lys Tyr Val Ser Leu Glu Gly Leu Ala Gln Pro Val Ala
            20                  25                  30 gtc ttc ttg gga gtc cct ttt gct aag cca cct ctt gga tct ttg agg     144
Val Phe Leu Gly Val Pro Phe Ala Lys Pro Pro Leu Gly Ser Leu Arg
        35                  40                  45 ttt gcc ccg ccg caa cca gca gag cca tgg tct ttc gtt aag aac act     192
Phe Ala Pro Pro Gln Pro Ala Glu Pro Trp Ser Phe Val Lys Asn Thr
    50                  55                  60 act tcc tac cct cca atg tgt tgt caa gat cca gtc gta gaa caa atg     240
Thr Ser Tyr Pro Pro Met Cys Cys Gln Asp Pro Val Val Glu Gln Met
65                  70                  75                  80 acg tca gac cta ttc act aac gga aag gaa agg ctt acc ctg gag ttc     288
Thr Ser Asp Leu Phe Thr Asn Gly Lys Glu Arg Leu Thr Leu Glu Phe
                85                  90                  95 tct gag gat tgc ctt tac cta aat att tac act cct gcc gat ttg aca     336
Ser Glu Asp Cys Leu Tyr Leu Asn Ile Tyr Thr Pro Ala Asp Leu Thr
            100                 105                 110 aag agg ggt agg ttg ccg gtt atg gtt tgg att cat gga gga ggt ttg     384
Lys Arg Gly Arg Leu Pro Val Met Val Trp Ile His Gly Gly Gly Leu
        115                 120                 125 gtt gtt ggc gga gca tcc act tat gac gga ttg gct ctt gcc gcg cac     432
Val Val Gly Gly Ala Ser Thr Tyr Asp Gly Leu Ala Leu Ala Ala His
    130                 135                 140 gag aac gtt gtt gtt gtt gct att caa tac cgt ttg ggt att tgg gga     480
Glu Asn Val Val Val Val Ala Ile Gln Tyr Arg Leu Gly Ile Trp Gly
145                 150                 155                 160 ttt ttc tcc aca gga gat gag cat tcc cgt gga aac tgg ggc cat tta     528
Phe Phe Ser Thr Gly Asp Glu His Ser Arg Gly Asn Trp Gly His Leu
                165                 170                 175 gat caa gtt gct gca ttg cat tgg gtc caa gaa aac att gct aac ttc     576
Asp Gln Val Ala Ala Leu His Trp Val Gln Glu Asn Ile Ala Asn Phe
            180                 185                 190 gga ggt gat cca ggt tct gtt act att ttc gga gaa tca gca ggc gga     624
Gly Gly Asp Pro Gly Ser Val Thr Ile Phe Gly Glu Ser Ala Gly Gly
        195                 200                 205 gag agt gtc tct gta ttg gtt tta tca cca tta gct aag aac ctt ttt     672
Glu Ser Val Ser Val Leu Val Leu Ser Pro Leu Ala Lys Asn Leu Phe
    210                 215                 220 cat cgt gct att tcc gaa agt ggt gtt gct ttt acc gcc ggt ttg gtc     720
His Arg Ala Ile Ser Glu Ser Gly Val Ala Phe Thr Ala Gly Leu Val
225                 230                 235                 240
```

| | | |
|---|---|---|
| agg aag gat atg aag gcc gca gcc aag cag atc gct gtc ctt gca gga<br>Arg Lys Asp Met Lys Ala Ala Ala Lys Gln Ile Ala Val Leu Ala Gly<br>                245                        250                        255 | | 768 |
| tgc aaa act act act tcg gca gtc ttc gtg cat tgt ttg cgt caa aag<br>Cys Lys Thr Thr Thr Ser Ala Val Phe Val His Cys Leu Arg Gln Lys<br>            260                        265                        270 | | 816 |
| tcg gaa gat gaa ctt tta gac ctc acg ttg aag atg aaa ttc ttt gcc<br>Ser Glu Asp Glu Leu Leu Asp Leu Thr Leu Lys Met Lys Phe Phe Ala<br>    275                        280                        285 | | 864 |
| ctt gac tta cac gga gat cca agg gaa tct cac cct ttt ttg acc act<br>Leu Asp Leu His Gly Asp Pro Arg Glu Ser His Pro Phe Leu Thr Thr<br>        290                        295                        300 | | 912 |
| gtt gtt gac gga gtt ttg ttg cct aag atg cct gag gaa atc ttg gcc<br>Val Val Asp Gly Val Leu Leu Pro Lys Met Pro Glu Glu Ile Leu Ala<br>305                        310                        315                        320 | | 960 |
| gag aag gac ttt aac acc gtc cca tac att gtt gga att aac aag cag<br>Glu Lys Asp Phe Asn Thr Val Pro Tyr Ile Val Gly Ile Asn Lys Gln<br>                325                        330                        335 | | 1008 |
| gag ttc gga tgg ctt ttg cca acg atg atg gga ttt cct ctt tcc gag<br>Glu Phe Gly Trp Leu Leu Pro Thr Met Met Gly Phe Pro Leu Ser Glu<br>            340                        345                        350 | | 1056 |
| gga aag ttg gat caa aag acg gct acg tca ctt ttg tgg aag tcc tac<br>Gly Lys Leu Asp Gln Lys Thr Ala Thr Ser Leu Leu Trp Lys Ser Tyr<br>    355                        360                        365 | | 1104 |
| cca att gcc aac att cct gaa gag ttg acc cca gtt gct acc gat aag<br>Pro Ile Ala Asn Ile Pro Glu Glu Leu Thr Pro Val Ala Thr Asp Lys<br>        370                        375                        380 | | 1152 |
| tat tta gga gga aca gat gat cct gtc aaa aag aaa gat ttg ttt ttg<br>Tyr Leu Gly Gly Thr Asp Asp Pro Val Lys Lys Lys Asp Leu Phe Leu<br>385                        390                        395                        400 | | 1200 |
| gat ctg atg gga gac gtt gtt ttc ggc gtc cca tca gtt acg gtt gct<br>Asp Leu Met Gly Asp Val Val Phe Gly Val Pro Ser Val Thr Val Ala<br>                405                        410                        415 | | 1248 |
| cgt cag cat agg gac gca gga gct cca act tac atg tat gag ttc caa<br>Arg Gln His Arg Asp Ala Gly Ala Pro Thr Tyr Met Tyr Glu Phe Gln<br>            420                        425                        430 | | 1296 |
| tat cgt cca tct ttt tca tcg gat aag aaa cct aag acg gtt att gga<br>Tyr Arg Pro Ser Phe Ser Ser Asp Lys Lys Pro Lys Thr Val Ile Gly<br>    435                        440                        445 | | 1344 |
| gat cat gga gac gaa att ttt tcc gtc ttc ggc ttc cca ttg ctc aaa<br>Asp His Gly Asp Glu Ile Phe Ser Val Phe Gly Phe Pro Leu Leu Lys<br>        450                        455                        460 | | 1392 |
| ggt gac gct cca gag gaa gaa gtc agt ctt tct aag acg gtt atg aaa<br>Gly Asp Ala Pro Glu Glu Glu Val Ser Leu Ser Lys Thr Val Met Lys<br>465                        470                        475                        480 | | 1440 |
| ttt tgg gct aac ttc gcc cgt agt gga aac cct aat gga gaa gga ttg<br>Phe Trp Ala Asn Phe Ala Arg Ser Gly Asn Pro Asn Gly Glu Gly Leu<br>                485                        490                        495 | | 1488 |
| cct cac tgg ccg atg tac gat caa gag gag gga tac ctt caa att ggt<br>Pro His Trp Pro Met Tyr Asp Gln Glu Glu Gly Tyr Leu Gln Ile Gly<br>            500                        505                        510 | | 1536 |
| gtc aac act caa gca gct aag agg ttg aaa ggc gag gag gtt gct ttt<br>Val Asn Thr Gln Ala Ala Lys Arg Leu Lys Gly Glu Glu Val Ala Phe<br>    515                        520                        525 | | 1584 |
| tgg aac gac ctg ttg tcc aag gaa gca gca aag aag cca cct aag ata<br>Trp Asn Asp Leu Leu Ser Lys Glu Ala Ala Lys Lys Pro Pro Lys Ile<br>        530                        535                        540 | | 1632 |
| aag cac gcc gaa ttg taa<br>Lys His Ala Glu Leu | | 1650 |

-continued

<210> SEQ ID NO 8
<211> LENGTH: 549
<212> TYPE: PRT
<213> ORGANISM: artificial sequence
<220> FEATURE:
<223> OTHER INFORMATION: Synthetic Construct

<400> SEQUENCE: 8

```
Met Gly Gln Pro Ala Ser Pro Pro Val Val Asp Thr Ala Gln Gly Arg
1               5                   10                  15

Val Leu Gly Lys Tyr Val Ser Leu Glu Gly Leu Ala Gln Pro Val Ala
            20                  25                  30

Val Phe Leu Gly Val Pro Phe Ala Lys Pro Pro Leu Gly Ser Leu Arg
        35                  40                  45

Phe Ala Pro Pro Gln Pro Ala Glu Pro Trp Ser Phe Val Lys Asn Thr
    50                  55                  60

Thr Ser Tyr Pro Pro Met Cys Cys Gln Asp Pro Val Val Glu Gln Met
65                  70                  75                  80

Thr Ser Asp Leu Phe Thr Asn Gly Lys Glu Arg Leu Thr Leu Glu Phe
                85                  90                  95

Ser Glu Asp Cys Leu Tyr Leu Asn Ile Tyr Thr Pro Ala Asp Leu Thr
            100                 105                 110

Lys Arg Gly Arg Leu Pro Val Met Val Trp Ile His Gly Gly Gly Leu
        115                 120                 125

Val Val Gly Gly Ala Ser Thr Tyr Asp Gly Leu Ala Leu Ala Ala His
    130                 135                 140

Glu Asn Val Val Val Ala Ile Gln Tyr Arg Leu Gly Ile Trp Gly
145                 150                 155                 160

Phe Phe Ser Thr Gly Asp Glu His Ser Arg Gly Asn Trp Gly His Leu
                165                 170                 175

Asp Gln Val Ala Ala Leu His Trp Val Gln Glu Asn Ile Ala Asn Phe
            180                 185                 190

Gly Gly Asp Pro Gly Ser Val Thr Ile Phe Gly Glu Ser Ala Gly Gly
        195                 200                 205

Glu Ser Val Ser Val Leu Val Leu Ser Pro Leu Ala Lys Asn Leu Phe
    210                 215                 220

His Arg Ala Ile Ser Glu Ser Gly Val Ala Phe Thr Ala Gly Leu Val
225                 230                 235                 240

Arg Lys Asp Met Lys Ala Ala Lys Gln Ile Ala Val Leu Ala Gly
                245                 250                 255

Cys Lys Thr Thr Thr Ser Ala Val Phe Val His Cys Leu Arg Gln Lys
                260                 265                 270

Ser Glu Asp Glu Leu Leu Asp Leu Thr Leu Lys Met Lys Phe Phe Ala
        275                 280                 285

Leu Asp Leu His Gly Asp Pro Arg Glu Ser His Pro Phe Leu Thr Thr
    290                 295                 300

Val Val Asp Gly Val Leu Leu Pro Lys Met Pro Glu Glu Ile Leu Ala
305                 310                 315                 320

Glu Lys Asp Phe Asn Thr Val Pro Tyr Ile Val Gly Ile Asn Lys Gln
                325                 330                 335

Glu Phe Gly Trp Leu Leu Pro Thr Met Met Gly Phe Pro Leu Ser Glu
            340                 345                 350

Gly Lys Leu Asp Gln Lys Thr Ala Thr Ser Leu Leu Trp Lys Ser Tyr
```

-continued

```
                355                 360                 365
Pro Ile Ala Asn Ile Pro Glu Glu Leu Thr Pro Val Ala Thr Asp Lys
                370                 375                 380

Tyr Leu Gly Gly Thr Asp Pro Val Lys Lys Asp Leu Phe Leu
385                 390                 395                 400

Asp Leu Met Gly Asp Val Val Phe Gly Val Pro Ser Val Thr Val Ala
                    405                 410                 415

Arg Gln His Arg Asp Ala Gly Ala Pro Thr Tyr Met Tyr Glu Phe Gln
                420                 425                 430

Tyr Arg Pro Ser Phe Ser Ser Asp Lys Lys Pro Lys Thr Val Ile Gly
            435                 440                 445

Asp His Gly Asp Glu Ile Phe Ser Val Phe Gly Phe Pro Leu Leu Lys
        450                 455                 460

Gly Asp Ala Pro Glu Glu Val Ser Leu Ser Lys Thr Val Met Lys
465                 470                 475                 480

Phe Trp Ala Asn Phe Ala Arg Ser Gly Asn Pro Asn Gly Glu Gly Leu
                    485                 490                 495

Pro His Trp Pro Met Tyr Asp Gln Glu Glu Gly Tyr Leu Gln Ile Gly
                500                 505                 510

Val Asn Thr Gln Ala Ala Lys Arg Leu Lys Gly Glu Val Ala Phe
            515                 520                 525

Trp Asn Asp Leu Leu Ser Lys Glu Ala Ala Lys Lys Pro Pro Lys Ile
530                 535                 540

Lys His Ala Glu Leu
545

<210> SEQ ID NO 9
<211> LENGTH: 1650
<212> TYPE: DNA
<213> ORGANISM: artificial sequence
<220> FEATURE:
<223> OTHER INFORMATION: gene PLE variant SEQ ID No. 10, codon optimized
<220> FEATURE:
<221> NAME/KEY: CDS
<222> LOCATION: (1)..(1650)
<223> OTHER INFORMATION: PLE variant

<400> SEQUENCE: 9 atg gga caa cca gct tcg ccg cct gtc gtt gat acc gct caa gga cga      48
Met Gly Gln Pro Ala Ser Pro Pro Val Val Asp Thr Ala Gln Gly Arg
1               5                   10                  15 gtc ttg ggt aag tac gtc tct tta gag gga ttg gca caa ccg gtt gct      96
Val Leu Gly Lys Tyr Val Ser Leu Glu Gly Leu Ala Gln Pro Val Ala
                20                  25                  30 gtc ttc ttg gga gtc cct ttt gct aag cca cct ctt gga tct ttg agg     144
Val Phe Leu Gly Val Pro Phe Ala Lys Pro Pro Leu Gly Ser Leu Arg
            35                  40                  45 ttt gcc ccg ccg caa cca gca gag cca tgg tct ttc gtt aag aac act     192
Phe Ala Pro Pro Gln Pro Ala Glu Pro Trp Ser Phe Val Lys Asn Thr
        50                  55                  60 act tcc tac cct cca atg tgt tgt caa gaa cca atc gga gga caa atg     240
Thr Ser Tyr Pro Pro Met Cys Cys Gln Glu Pro Ile Gly Gly Gln Met
65                  70                  75                  80 ctt tca gac cta ttc act aac aga aag gaa agg ctt atc ccg gag ttc     288
Leu Ser Asp Leu Phe Thr Asn Arg Lys Glu Arg Leu Ile Pro Glu Phe
                85                  90                  95 tct gag gat tgc ctt tac cta aat att tac act cct gcc gat ttg aca     336
Ser Glu Asp Cys Leu Tyr Leu Asn Ile Tyr Thr Pro Ala Asp Leu Thr
                100                 105                 110
```

```
aag agg ggt agg ttg ccg gtt atg gtt tgg att cat gga gga ggt ttg        384
Lys Arg Gly Arg Leu Pro Val Met Val Trp Ile His Gly Gly Gly Leu
        115                 120                 125 gtt gtt ggc gga gca tcc act tat gac gga ttg gct ctt gcc gcg cac        432
Val Val Gly Gly Ala Ser Thr Tyr Asp Gly Leu Ala Leu Ala Ala His
130                 135                 140 gag aac gtt gtt gtt gtt gct att caa tac cgt ttg ggt att tgg gga        480
Glu Asn Val Val Val Val Ala Ile Gln Tyr Arg Leu Gly Ile Trp Gly
145                 150                 155                 160 ttt ttc tcc aca gga gat gag cat tcc cgt gga aac tgg ggc cat tta        528
Phe Phe Ser Thr Gly Asp Glu His Ser Arg Gly Asn Trp Gly His Leu
                165                 170                 175 gat caa gtt gct gca ttg cat tgg gtc caa gaa aac att gct aac ttc        576
Asp Gln Val Ala Ala Leu His Trp Val Gln Glu Asn Ile Ala Asn Phe
        180                 185                 190 gga ggt gat cca ggt tct gtt act att ttc gga gaa tca gca ggc gga        624
Gly Gly Asp Pro Gly Ser Val Thr Ile Phe Gly Glu Ser Ala Gly Gly
            195                 200                 205 gag agt gtc tct gta ttg gtt tta tca cca tta gct aag aac ctt ttt        672
Glu Ser Val Ser Val Leu Val Leu Ser Pro Leu Ala Lys Asn Leu Phe
210                 215                 220 cat cgt gct att tcc gaa agt ggt gtt gct ttt acc gcc ggt ttg gtc        720
His Arg Ala Ile Ser Glu Ser Gly Val Ala Phe Thr Ala Gly Leu Val
225                 230                 235                 240 agg aag gat atg aag gcc gca gcc aag cag atc gct gtc ctt gca gga        768
Arg Lys Asp Met Lys Ala Ala Ala Lys Gln Ile Ala Val Leu Ala Gly
                245                 250                 255 tgc aaa act act act tcg gca gac ttc gtg cat tgt ttg cgt caa aag        816
Cys Lys Thr Thr Thr Ser Ala Asp Phe Val His Cys Leu Arg Gln Lys
        260                 265                 270 tcg gaa gat gaa ctt tta gac ctc acg ttg aag atg aaa ttc ttt gcc        864
Ser Glu Asp Glu Leu Leu Asp Leu Thr Leu Lys Met Lys Phe Phe Ala
            275                 280                 285 ctt gac tta cac gga gat cca agg gaa tct cac cct ttt ttg acc act        912
Leu Asp Leu His Gly Asp Pro Arg Glu Ser His Pro Phe Leu Thr Thr
290                 295                 300 gtt gtt gac gga gtt ttg ttg cct aag atg cct gag gaa atc ttg gcc        960
Val Val Asp Gly Val Leu Leu Pro Lys Met Pro Glu Glu Ile Leu Ala
305                 310                 315                 320 gag aag gac ttt aac acc gtc cca tac att gtt gga att aac aag cag       1008
Glu Lys Asp Phe Asn Thr Val Pro Tyr Ile Val Gly Ile Asn Lys Gln
                325                 330                 335 gag ttc gga tgg ctt ttg cca acg atg atg gga ttt cct ctt tcc gag       1056
Glu Phe Gly Trp Leu Leu Pro Thr Met Met Gly Phe Pro Leu Ser Glu
        340                 345                 350 gga aag ttg gat caa aag acg gct acg tca ctt ttg tgg aag tcc tac       1104
Gly Lys Leu Asp Gln Lys Thr Ala Thr Ser Leu Leu Trp Lys Ser Tyr
            355                 360                 365 cca att gcc aac att cct gaa gag ttg acc cca gtt gct acc gat aag       1152
Pro Ile Ala Asn Ile Pro Glu Glu Leu Thr Pro Val Ala Thr Asp Lys
370                 375                 380 tat tta gga gga aca gat gat cct gtc aaa aag aaa gat ttg ttt ttg       1200
Tyr Leu Gly Gly Thr Asp Asp Pro Val Lys Lys Lys Asp Leu Phe Leu
385                 390                 395                 400 gat ctg atg gga gac gtt gtt ttc ggc gtc cca tca gtt acg gtt gct       1248
Asp Leu Met Gly Asp Val Val Phe Gly Val Pro Ser Val Thr Val Ala
                405                 410                 415 cgt cag cat agg gac gca gga gct cca act tac atg tat gag ttc caa       1296
Arg Gln His Arg Asp Ala Gly Ala Pro Thr Tyr Met Tyr Glu Phe Gln
```

```
                    420                 425                 430
tat cgt cca tct ttt tca tcg gat aag aaa cct aag acg gtt att gga      1344
Tyr Arg Pro Ser Phe Ser Ser Asp Lys Lys Pro Lys Thr Val Ile Gly
        435                 440                 445 gat cat gga gac gaa att ttt tcc gtc ttc ggc ttc cca ttg ctc aaa      1392
Asp His Gly Asp Glu Ile Phe Ser Val Phe Gly Phe Pro Leu Leu Lys
450                 455                 460 ggt gac gct cca gag gaa gaa gtc agt ctt tct aag acg gtt atg aaa      1440
Gly Asp Ala Pro Glu Glu Glu Val Ser Leu Ser Lys Thr Val Met Lys
465                 470                 475                 480 ttt tgg gct aac ttc gcc cgt agt gga aac cct aat gga gaa gga ttg      1488
Phe Trp Ala Asn Phe Ala Arg Ser Gly Asn Pro Asn Gly Glu Gly Leu
                485                 490                 495 cct cac tgg ccg atg tac gat caa gag gag gga tac ctt caa att ggt      1536
Pro His Trp Pro Met Tyr Asp Gln Glu Glu Gly Tyr Leu Gln Ile Gly
            500                 505                 510 gtc aac act caa gca gct aag agg ttg aaa ggc gag gag gtt gct ttt      1584
Val Asn Thr Gln Ala Ala Lys Arg Leu Lys Gly Glu Glu Val Ala Phe
        515                 520                 525 tgg aac gac ctg ttg tcc aag gaa gca gca aag aag cca cct aag ata      1632
Trp Asn Asp Leu Leu Ser Lys Glu Ala Ala Lys Lys Pro Pro Lys Ile
530                 535                 540 aag cac gcc gaa ttg taa                                              1650
Lys His Ala Glu Leu
545

<210> SEQ ID NO 10
<211> LENGTH: 549
<212> TYPE: PRT
<213> ORGANISM: artificial sequence
<220> FEATURE:
<223> OTHER INFORMATION: Synthetic Construct

<400> SEQUENCE: 10

Met Gly Gln Pro Ala Ser Pro Val Val Asp Thr Ala Gln Gly Arg
1               5                   10                  15

Val Leu Gly Lys Tyr Val Ser Leu Glu Gly Leu Ala Gln Pro Val Ala
                20                  25                  30

Val Phe Leu Gly Val Pro Phe Ala Lys Pro Pro Leu Gly Ser Leu Arg
            35                  40                  45

Phe Ala Pro Pro Gln Pro Ala Glu Pro Trp Ser Phe Val Lys Asn Thr
        50                  55                  60

Thr Ser Tyr Pro Pro Met Cys Cys Gln Glu Pro Ile Gly Gly Gln Met
65                  70                  75                  80

Leu Ser Asp Leu Phe Thr Asn Arg Lys Glu Arg Leu Ile Pro Glu Phe
                85                  90                  95

Ser Glu Asp Cys Leu Tyr Leu Asn Ile Tyr Thr Pro Ala Asp Leu Thr
            100                 105                 110

Lys Arg Gly Arg Leu Pro Val Met Val Trp Ile His Gly Gly Gly Leu
        115                 120                 125

Val Val Gly Gly Ala Ser Thr Tyr Asp Gly Leu Ala Leu Ala Ala His
130                 135                 140

Glu Asn Val Val Val Ala Ile Gln Tyr Arg Leu Gly Ile Trp Gly
145                 150                 155                 160

Phe Phe Ser Thr Gly Asp Glu His Ser Arg Gly Asn Trp Gly His Leu
                165                 170                 175

Asp Gln Val Ala Ala Leu His Trp Val Gln Glu Asn Ile Ala Asn Phe
            180                 185                 190
```

Gly Gly Asp Pro Gly Ser Val Thr Ile Phe Gly Glu Ser Ala Gly Gly
            195                 200                 205

Glu Ser Val Ser Val Leu Val Leu Ser Pro Leu Ala Lys Asn Leu Phe
        210                 215                 220

His Arg Ala Ile Ser Glu Ser Gly Val Ala Phe Thr Ala Gly Leu Val
225                 230                 235                 240

Arg Lys Asp Met Lys Ala Ala Lys Gln Ile Ala Val Leu Ala Gly
                245                 250                 255

Cys Lys Thr Thr Thr Ser Ala Asp Phe Val His Cys Leu Arg Gln Lys
                260                 265                 270

Ser Glu Asp Glu Leu Leu Asp Leu Thr Leu Lys Met Lys Phe Phe Ala
        275                 280                 285

Leu Asp Leu His Gly Asp Pro Arg Glu Ser His Pro Phe Leu Thr Thr
        290                 295                 300

Val Val Asp Gly Val Leu Leu Pro Lys Met Pro Glu Ile Leu Ala
305                 310                 315                 320

Glu Lys Asp Phe Asn Thr Val Pro Tyr Ile Val Gly Ile Asn Lys Gln
                325                 330                 335

Glu Phe Gly Trp Leu Leu Pro Thr Met Met Gly Phe Pro Leu Ser Glu
            340                 345                 350

Gly Lys Leu Asp Gln Lys Thr Ala Thr Ser Leu Leu Trp Lys Ser Tyr
        355                 360                 365

Pro Ile Ala Asn Ile Pro Glu Glu Leu Thr Pro Val Ala Thr Asp Lys
        370                 375                 380

Tyr Leu Gly Gly Thr Asp Asp Pro Val Lys Lys Asp Leu Phe Leu
385                 390                 395                 400

Asp Leu Met Gly Asp Val Val Phe Gly Val Pro Ser Val Thr Val Ala
                405                 410                 415

Arg Gln His Arg Asp Ala Gly Ala Pro Thr Tyr Met Tyr Glu Phe Gln
                420                 425                 430

Tyr Arg Pro Ser Phe Ser Ser Asp Lys Lys Pro Lys Thr Val Ile Gly
        435                 440                 445

Asp His Gly Asp Glu Ile Phe Ser Val Phe Gly Phe Pro Leu Leu Lys
        450                 455                 460

Gly Asp Ala Pro Glu Glu Glu Val Ser Leu Ser Lys Thr Val Met Lys
465                 470                 475                 480

Phe Trp Ala Asn Phe Ala Arg Ser Gly Asn Pro Asn Gly Glu Gly Leu
                485                 490                 495

Pro His Trp Pro Met Tyr Asp Gln Glu Gly Tyr Leu Gln Ile Gly
                500                 505                 510

Val Asn Thr Gln Ala Ala Lys Arg Leu Lys Gly Glu Glu Val Ala Phe
        515                 520                 525

Trp Asn Asp Leu Leu Ser Lys Glu Ala Ala Lys Lys Pro Pro Lys Ile
530                 535                 540

Lys His Ala Glu Leu
545

<210> SEQ ID NO 11
<211> LENGTH: 1650
<212> TYPE: DNA
<213> ORGANISM: artificial sequence
<220> FEATURE:
<223> OTHER INFORMATION: gene APLE Hybrid 4 SEQ ID No. 12, codon
      optimized
<220> FEATURE:

```
<221> NAME/KEY: CDS
<222> LOCATION: (1)..(1650)
<223> OTHER INFORMATION: APLE Hybrid 4

<400> SEQUENCE: 11 atg gga caa cca gct tcg ccg cct gtc gtt gat acc gct caa gga cga        48
Met Gly Gln Pro Ala Ser Pro Pro Val Val Asp Thr Ala Gln Gly Arg
1               5                   10                  15 gtc ttg ggt aag tac gtc tct tta gag gga ttg gca caa ccg gtt gct        96
Val Leu Gly Lys Tyr Val Ser Leu Glu Gly Leu Ala Gln Pro Val Ala
            20                  25                  30 gtc ttc ttg gga gtc cct ttt gct aag cca cct ctt gga tct ttg agg       144
Val Phe Leu Gly Val Pro Phe Ala Lys Pro Pro Leu Gly Ser Leu Arg
        35                  40                  45 ttt gcc ccg ccg caa cca gca gag cca tgg tct ttc gtt aag aac act       192
Phe Ala Pro Pro Gln Pro Ala Glu Pro Trp Ser Phe Val Lys Asn Thr
50                  55                  60 act tcc tac cct cca atg tgt tgt caa gaa cca atc gga gga caa atg       240
Thr Ser Tyr Pro Pro Met Cys Cys Gln Glu Pro Ile Gly Gly Gln Met
65                  70                  75                  80 ctt tca gac cta ttc act aac aga aag gaa agg ctt atc ccg gag ttc       288
Leu Ser Asp Leu Phe Thr Asn Arg Lys Glu Arg Leu Ile Pro Glu Phe
                85                  90                  95 tct gag gat tgc ctt tac cta aat att tac act cct gcc gat ttg aca       336
Ser Glu Asp Cys Leu Tyr Leu Asn Ile Tyr Thr Pro Ala Asp Leu Thr
            100                 105                 110 aag agg ggt agg ttg ccg gtt atg gtt tgg att cat gga gga ggt ttg       384
Lys Arg Gly Arg Leu Pro Val Met Val Trp Ile His Gly Gly Gly Leu
        115                 120                 125 gtt gtt ggc gga gca tcc act tat gac gga ttg gct ctt gcc gcg cac       432
Val Val Gly Gly Ala Ser Thr Tyr Asp Gly Leu Ala Leu Ala Ala His
130                 135                 140 gag aac gtt gtt gtt gtt gct att caa tac cgt ttg ggt att tgg gga       480
Glu Asn Val Val Val Val Ala Ile Gln Tyr Arg Leu Gly Ile Trp Gly
145                 150                 155                 160 ttt ttc tcc aca gga gat gag cat tcc cgt gga aac tgg ggc cat tta       528
Phe Phe Ser Thr Gly Asp Glu His Ser Arg Gly Asn Trp Gly His Leu
                165                 170                 175 gat caa gtt gct gca ttg cat tgg gtc caa gaa aac att gct aac ttc       576
Asp Gln Val Ala Ala Leu His Trp Val Gln Glu Asn Ile Ala Asn Phe
            180                 185                 190 gga ggt gat cca ggt tct gtt act att ttc gga gaa tca gca ggc gga       624
Gly Gly Asp Pro Gly Ser Val Thr Ile Phe Gly Glu Ser Ala Gly Gly
        195                 200                 205 gag agt gtc tct gta ttg gtt tta tca cca tta gct aag aac ctt ttt       672
Glu Ser Val Ser Val Leu Val Leu Ser Pro Leu Ala Lys Asn Leu Phe
210                 215                 220 cat cgt gct att tcc gaa agt ggt gtt gct ttt acc gcc ggt ttg gtc       720
His Arg Ala Ile Ser Glu Ser Gly Val Ala Phe Thr Ala Gly Leu Val
225                 230                 235                 240 agg aag gat atg aag gcc gca gcc aag cag atc gct gtc ctt gca gga       768
Arg Lys Asp Met Lys Ala Ala Ala Lys Gln Ile Ala Val Leu Ala Gly
                245                 250                 255 tgc aaa act act act tcg gca gtc ttc gtg cat tgt ttg cgt caa aag       816
Cys Lys Thr Thr Thr Ser Ala Val Phe Val His Cys Leu Arg Gln Lys
            260                 265                 270 tcg gaa gat gaa ctt tta gac ctc acg ttg aag atg aaa ttc ctg acc       864
Ser Glu Asp Glu Leu Leu Asp Leu Thr Leu Lys Met Lys Phe Leu Thr
        275                 280                 285 ctt gac ttt cac gga gat caa agg gaa tct cac cct ttt ttg ccg act       912
```

```
        Leu Asp Phe His Gly Asp Gln Arg Glu Ser His Pro Phe Leu Pro Thr
            290                 295                 300 gtt gtc gac gga gtt ttg ttg cct aag atg cct gag gaa atc ttg gcc        960
Val Val Asp Gly Val Leu Leu Pro Lys Met Pro Glu Glu Ile Leu Ala
305                 310                 315                 320 gag aag gac ttt aac acc gtc cca tac att gtt gga att aac aag cag       1008
Glu Lys Asp Phe Asn Thr Val Pro Tyr Ile Val Gly Ile Asn Lys Gln
                325                 330                 335 gag ttc gga tgg ctt ttg cca acg atg atg gga ttt cct ctt tcc gag       1056
Glu Phe Gly Trp Leu Leu Pro Thr Met Met Gly Phe Pro Leu Ser Glu
            340                 345                 350 gga aag ttg gat caa aag acg gct acg tca ctt ttg tgg aag tcc tac       1104
Gly Lys Leu Asp Gln Lys Thr Ala Thr Ser Leu Leu Trp Lys Ser Tyr
        355                 360                 365 cca att gcc aac att cct gaa gag ttg acc cca gtt gct acc gat aag       1152
Pro Ile Ala Asn Ile Pro Glu Glu Leu Thr Pro Val Ala Thr Asp Lys
    370                 375                 380 tat tta gga gga aca gat gat cct gtc aaa aag aaa gat ttg ttt ttg       1200
Tyr Leu Gly Gly Thr Asp Asp Pro Val Lys Lys Lys Asp Leu Phe Leu
385                 390                 395                 400 gat ctg atg gga gac gtt gtt ttc ggc gtc cca tca gtt acg gtt gct       1248
Asp Leu Met Gly Asp Val Val Phe Gly Val Pro Ser Val Thr Val Ala
                405                 410                 415 cgt cag cat agg gac gca gga gct cca act tac atg tat gag ttc caa       1296
Arg Gln His Arg Asp Ala Gly Ala Pro Thr Tyr Met Tyr Glu Phe Gln
            420                 425                 430 tat cgt cca tct ttt tca tcg gat aag aaa cct aag acg gtt att gga       1344
Tyr Arg Pro Ser Phe Ser Ser Asp Lys Lys Pro Lys Thr Val Ile Gly
        435                 440                 445 gat cat gga gac gaa att ttt tcc gtc ttc ggc ttc cca ttg ctc aaa       1392
Asp His Gly Asp Glu Ile Phe Ser Val Phe Gly Phe Pro Leu Leu Lys
    450                 455                 460 ggt gac gct cca gag gaa gaa gtc agt ctt tct aag acg gtt atg aaa       1440
Gly Asp Ala Pro Glu Glu Glu Val Ser Leu Ser Lys Thr Val Met Lys
465                 470                 475                 480 ttt tgg gct aac ttc gcc cgt agt gga aac cct aat gga gaa gga ttg       1488
Phe Trp Ala Asn Phe Ala Arg Ser Gly Asn Pro Asn Gly Glu Gly Leu
                485                 490                 495 cct cac tgg ccg atg tac gat caa gag gag gga tac ctt caa att ggt       1536
Pro His Trp Pro Met Tyr Asp Gln Glu Glu Gly Tyr Leu Gln Ile Gly
            500                 505                 510 gtc aac act caa gca gct aag agg ttg aaa ggc gag gag gtt gct ttt       1584
Val Asn Thr Gln Ala Ala Lys Arg Leu Lys Gly Glu Glu Val Ala Phe
        515                 520                 525 tgg aac gac ctg ttg tcc aag gaa gca gca aag aag cca cct aag ata       1632
Trp Asn Asp Leu Leu Ser Lys Glu Ala Ala Lys Lys Pro Pro Lys Ile
    530                 535                 540 aag cac gcc gaa ttg taa                                               1650
Lys His Ala Glu Leu
545

<210> SEQ ID NO 12
<211> LENGTH: 549
<212> TYPE: PRT
<213> ORGANISM: artificial sequence
<220> FEATURE:
<223> OTHER INFORMATION: Synthetic Construct

<400> SEQUENCE: 12

Met Gly Gln Pro Ala Ser Pro Val Val Asp Thr Ala Gln Gly Arg
1               5                   10                  15
```

Val Leu Gly Lys Tyr Val Ser Leu Glu Gly Leu Ala Gln Pro Val Ala
             20                  25                  30

Val Phe Leu Gly Val Pro Phe Ala Lys Pro Pro Leu Gly Ser Leu Arg
         35                  40                  45

Phe Ala Pro Pro Gln Pro Ala Glu Pro Trp Ser Phe Val Lys Asn Thr
 50                  55                  60

Thr Ser Tyr Pro Pro Met Cys Cys Gln Glu Pro Ile Gly Gly Gln Met
 65                  70                  75                  80

Leu Ser Asp Leu Phe Thr Asn Arg Lys Glu Arg Leu Ile Pro Glu Phe
                 85                  90                  95

Ser Glu Asp Cys Leu Tyr Leu Asn Ile Tyr Thr Pro Ala Asp Leu Thr
             100                 105                 110

Lys Arg Gly Arg Leu Pro Val Met Val Trp Ile His Gly Gly Gly Leu
         115                 120                 125

Val Val Gly Gly Ala Ser Thr Tyr Asp Gly Leu Ala Leu Ala Ala His
130                 135                 140

Glu Asn Val Val Val Ala Ile Gln Tyr Arg Leu Gly Ile Trp Gly
145                 150                 155                 160

Phe Phe Ser Thr Gly Asp Glu His Ser Arg Gly Asn Trp Gly His Leu
                 165                 170                 175

Asp Gln Val Ala Ala Leu His Trp Val Gln Glu Asn Ile Ala Asn Phe
             180                 185                 190

Gly Gly Asp Pro Gly Ser Val Thr Ile Phe Gly Glu Ser Ala Gly Gly
         195                 200                 205

Glu Ser Val Ser Val Leu Val Leu Ser Pro Leu Ala Lys Asn Leu Phe
210                 215                 220

His Arg Ala Ile Ser Glu Ser Gly Val Ala Phe Thr Ala Gly Leu Val
225                 230                 235                 240

Arg Lys Asp Met Lys Ala Ala Lys Gln Ile Ala Val Leu Ala Gly
                 245                 250                 255

Cys Lys Thr Thr Thr Ser Ala Val Phe Val His Cys Leu Arg Gln Lys
             260                 265                 270

Ser Glu Asp Glu Leu Leu Asp Leu Thr Leu Lys Met Lys Phe Leu Thr
         275                 280                 285

Leu Asp Phe His Gly Asp Gln Arg Glu Ser His Pro Phe Leu Pro Thr
290                 295                 300

Val Val Asp Gly Val Leu Leu Pro Lys Met Pro Glu Glu Ile Leu Ala
305                 310                 315                 320

Glu Lys Asp Phe Asn Thr Val Pro Tyr Ile Val Gly Ile Asn Lys Gln
                 325                 330                 335

Glu Phe Gly Trp Leu Leu Pro Thr Met Met Gly Phe Pro Leu Ser Glu
             340                 345                 350

Gly Lys Leu Asp Gln Lys Thr Ala Thr Ser Leu Leu Trp Lys Ser Tyr
         355                 360                 365

Pro Ile Ala Asn Ile Pro Glu Glu Leu Thr Pro Val Ala Thr Asp Lys
370                 375                 380

Tyr Leu Gly Gly Thr Asp Asp Pro Val Lys Lys Lys Asp Leu Phe Leu
385                 390                 395                 400

Asp Leu Met Gly Asp Val Val Phe Gly Val Pro Ser Val Thr Val Ala
                 405                 410                 415

Arg Gln His Arg Asp Ala Gly Ala Pro Thr Tyr Met Tyr Glu Phe Gln
             420                 425                 430

| | | | | | | | | | | | | |
|---|---|---|---|---|---|---|---|---|---|---|---|---|
| Tyr | Arg | Pro | Ser | Phe | Ser | Ser | Asp | Lys | Lys | Pro | Lys | Thr | Val | Ile | Gly |
| | | 435 | | | | 440 | | | | | 445 | | | | |
| Asp | His | Gly | Asp | Glu | Ile | Phe | Ser | Val | Phe | Gly | Phe | Pro | Leu | Leu | Lys |
| | | 450 | | | | | 455 | | | | | 460 | | | |
| Gly | Asp | Ala | Pro | Glu | Glu | Glu | Val | Ser | Leu | Ser | Lys | Thr | Val | Met | Lys |
| 465 | | | | | 470 | | | | | 475 | | | | | 480 |
| Phe | Trp | Ala | Asn | Phe | Ala | Arg | Ser | Gly | Asn | Pro | Asn | Gly | Glu | Gly | Leu |
| | | | | 485 | | | | | 490 | | | | | 495 | |
| Pro | His | Trp | Pro | Met | Tyr | Asp | Gln | Glu | Glu | Gly | Tyr | Leu | Gln | Ile | Gly |
| | | | 500 | | | | | 505 | | | | | 510 | | |
| Val | Asn | Thr | Gln | Ala | Ala | Lys | Arg | Leu | Lys | Gly | Glu | Glu | Val | Ala | Phe |
| | | 515 | | | | | 520 | | | | | 525 | | | |
| Trp | Asn | Asp | Leu | Leu | Ser | Lys | Glu | Ala | Ala | Lys | Lys | Pro | Pro | Lys | Ile |
| | 530 | | | | | 535 | | | | | 540 | | | | |
| Lys | His | Ala | Glu | Leu |
| 545 | | | | |